United States Patent
Chu et al.

(10) Patent No.: US 10,301,365 B2
(45) Date of Patent: May 28, 2019

(54) MET E 1 TROPOMYOSIN VARIANTS FOR USE IN ALLERGEN-SPECIFIC IMMUNOTHERAPY

(71) Applicants: The Chinese University of Hong Kong, Shatin, N.T., Hong Kong SAR (CN); The Regents of the University of California, Oakland, CA (US)

(72) Inventors: Ka Hou Chu, Hong Kong SAR (CN); Patrick S. C. Leung, Davis, CA (US); Yee Yan Christine Wai, Hong Kong SAR (CN); Yat Hin Nicki Leung, Hong Kong SAR (CN)

(73) Assignees: The Chinese University of Hong Kong, Shatin, N.T., Hong Kong SAR (HK); The Regents of the University of California, Oakland, CA (US)

( * ) Notice: Subject to any disclaimer, the term of this patent is extended or adjusted under 35 U.S.C. 154(b) by 49 days.

(21) Appl. No.: 15/284,205

(22) Filed: Oct. 3, 2016

(65) Prior Publication Data
US 2017/0107265 A1   Apr. 20, 2017

Related U.S. Application Data

(60) Provisional application No. 62/241,476, filed on Oct. 14, 2015.

(51) Int. Cl.
| | |
|---|---|
| *A61K 48/00* | (2006.01) |
| *C07K 14/435* | (2006.01) |
| *C12N 15/09* | (2006.01) |
| *C12N 15/12* | (2006.01) |
| *C12N 15/63* | (2006.01) |
| *C12N 15/74* | (2006.01) |
| *C12N 15/79* | (2006.01) |
| *C07K 14/47* | (2006.01) |
| *A61K 38/17* | (2006.01) |
| *A61K 9/00* | (2006.01) |
| *A61K 38/00* | (2006.01) |

(52) U.S. Cl.
CPC ............ *C07K 14/47* (2013.01); *A61K 9/0019* (2013.01); *A61K 9/0053* (2013.01); *A61K 38/1709* (2013.01); *C07K 14/43509* (2013.01); *A61K 38/00* (2013.01)

(58) Field of Classification Search
CPC .... C07K 14/47; A61K 9/0019; A61K 9/0053; A61K 38/1709
See application file for complete search history.

(56) References Cited

U.S. PATENT DOCUMENTS

| | | | |
|---|---|---|---|
| 2011/0020373 A1* | 1/2011 | Saxon | A61K 39/00 424/181.1 |
| 2016/0355555 A1* | 12/2016 | Leung | C07K 14/43509 |

OTHER PUBLICATIONS

Chung-Faye et al., (Mol Med Today Feb. 2000 (6):82-87). (Year: 2000).*
Verma, et al., (Nature. Sep. 18, 1987 389:239-242). (Year: 1987).*
Juengst, (BMJ Jun. 28, 2003;326(7404):1410-1). (Year: 2003).*
Tait et al., (Clin.Canc.Res., vol. 5, Jul. 1999, pp. 1708-1714) (Year: 1999).*
Wai et al., (PLoS One. 2014;9(11):e111649 (10 pages) (ePub Nov. 3, 2014). (Year: 2014).*
Hochreiter et al., "Prevention of Allergen-Specific IgE Production and Suppression of an Established Th2-type Response by Immunization with DNA Encoding Hypoallergenic Allergen Derivatives of Bet v 1, the Major Birch-Pollen Allergen," Eur. J. Immunol. 2003, 33, 1667-1676.
Leung et al., "Cloning, Expression, and Primary Structure of *Metapenaeus ensis* Tropomyosin, the Major Heat-Stable Shrimp Allergen," J. Allergy Clin Immunol 1994; 94:882-90.
Leung et al., "Induction of Shrimp Tropomyosin-Specific Hypersensitivity in Mice," Int Arch Allergy Immunol 2008;147:305-314.
Reese, et al., "Reduced Alerginic Potency of VR9-1, a Mutant of the Major Shrimp Allergen Pen a 1 (Tropomyosin)," J. Immunol. 2005;175;8354-8364.

* cited by examiner

*Primary Examiner* — Michael D Pak
(74) *Attorney, Agent, or Firm* — Kilpatrick Townsedn & Stockton LLP

(57) ABSTRACT

The present invention provides isolated Met e 1 polypeptides and nucleic acids encoding the isolated polypeptides that can prevent and/or alleviate an allergic response to shellfish tropomyosin. The polypeptides are based on the shrimp tropomyosin Met e 1 protein and have been modified to act as hypoallergens. The Met e 1 hypoallergens have low to no IgE reactivity or allergenicity and are useful for prophylactic and/or therapeutic treatment of shellfish allergy in subject in need thereof.

20 Claims, 14 Drawing Sheets
Specification includes a Sequence Listing.

```
ATGAAATTAGAGAAAGATAATGCGATGGACCGCGCTGATACCGCTGAGG
GAGACAAAAAGGAGGCCAATAACCGCGCAGAGAAGTCTGAAGAAGAATT
AGTGGCGCTGCAGAAGAAATTGAAAGGCACCGAAGATGAACTGGATAAG
TATCAGGAAAGCCTGCTGAAGGCTAATAATCAGTTAGTGGAGAAGGATA
AGGCGCTGAGCAATGCGGAAGGCGAAGTGGCGAGCCTGAATCGTCGTA
TTCAGCTGGTCGAGGAAGAGCTGGATCGTGCACAGGAACGCTTAAATAC
CGCGACCACCAAACTGGCGGAAGCGAGCCAAGCAGCAGACGAGAGCGA
GCGTATGCGTAAAGTGCTTGAAAACCGTAGCCTGAGCGATGAAGAACGT
ATGGATGCGCTGGAAATTCAGTTAAAAGAAGCGAAACATATTGCTGAGG
AAGCGGATCGTAAATATGAGGAGGTTGCGCGTAAACTTGCTATGGTGGA
AGCAGATCTTGAACGGGCCGAGGAGCGTGCTGAAACCGGGGAAAGCAA
AATTAGCGAGCTTGAAGAGGAGTTGAAGACCGTGACGAACAATCTGAAA
AGTCTGGAAGCGCAAGCTGAGAAAGCTAACCAGCGGGAGGAGGCGTAT
AAAGAACAGATTAAAACCCTGACCAATAAACTGAAAGCGGCAGAAACCC
GTGCGGAATTTGCGGAACGTAGCGTGGCGAAACTGGAAAGACCATTGA
TGACCTGGAAGACGAACTGGTGAATGAAAAGAGAAATACAAAGCGATT
TCCGAAGAACTTGATCATGCACTGAATGATATGAGCGGCTAT
```

SEQ ID NO:1

Fig. 1

```
ATGAAGCTGGAGAAGGATAACGCCATGGACAGGGCGGATACCGAGGCC
AACAACAGGGCTGAGAAGAGCGAGGAGGAGCAGGAATCCTTGCTGAAG
GCAAACAACCAGCTCGTGGAGAAGGACAAGGCCCTCTCTAACGCTGAG
GGTGAGGTTGCTGAACGCCTCAACACCGCCACCACCAAGCTGGCTGAG
GCCTCCAGGCCGCCGACGAGTCCGAGCGCATGCGCAAGGTGCTCGA
GAACCGCTCCCTTTCCGATGAGGAGCGCATGGACGCCCTGGAGGCTGA
GGAAGCCGACAGGGCCCGTAAGCTGGCCATGGTTGAGGCCGACCTTGA
GCGTGCTGAAGAACGTGCTGAGACTGGTGAATCAAAGATCGAGAAGGCT
AACCAACGCGAAGAGGCCTACAAGGAGCAGATCAAGACCCTGACCAACA
AGCTGAAGGCGGCTTTCGCCGAGAGGTCTGTGCTCGAAGACGAACTGG
TTAACGAAAGGAGAAGTACAAGTCTGGCTAC
```

SEQ ID NO:2

Fig. 2

Fig. 6A
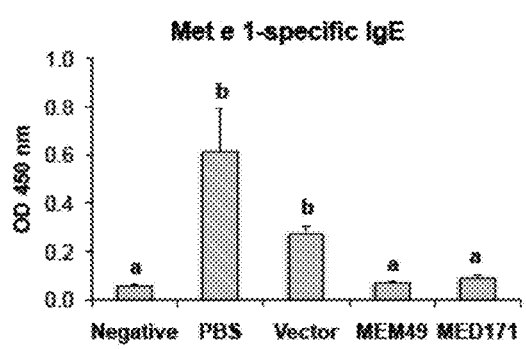
Fig. 6B
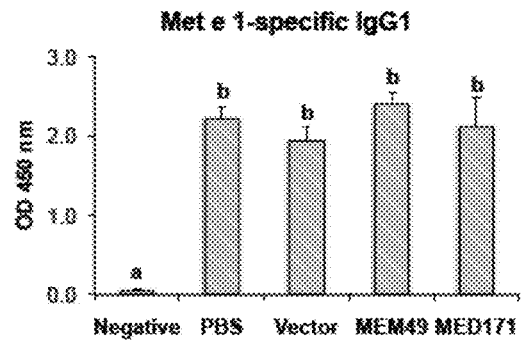
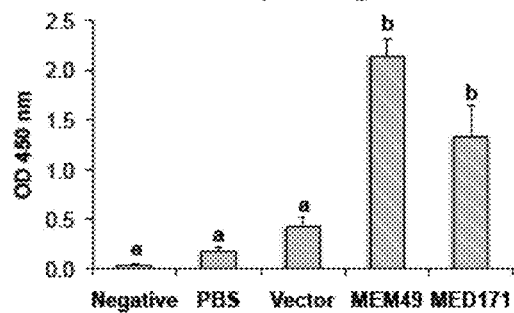
Fig. 6C
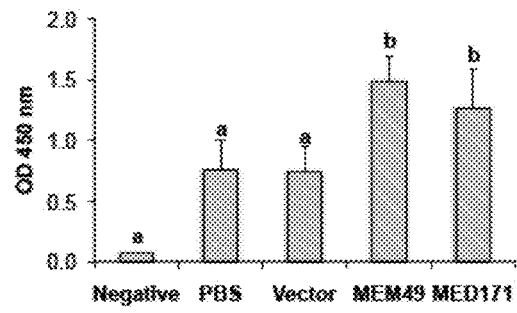
Fig. 6D

Fig. 7A
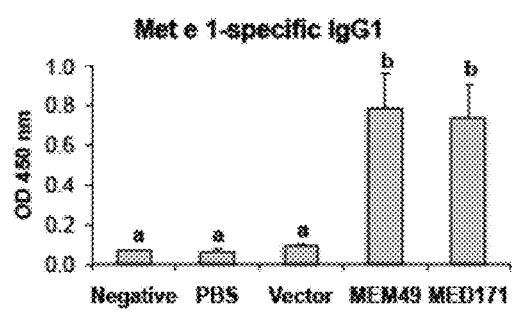
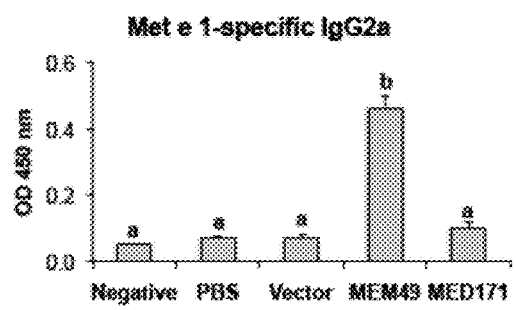
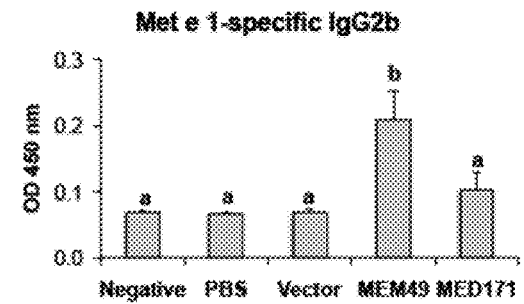
Fig. 7B
Fig. 7C

Fig. 12A
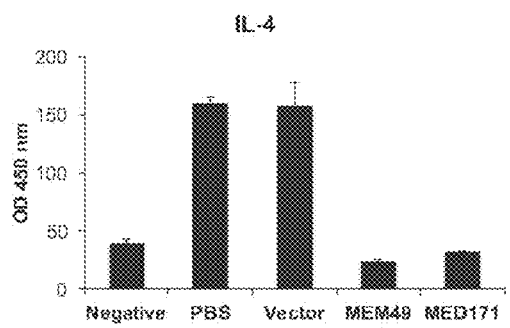
Fig. 12B
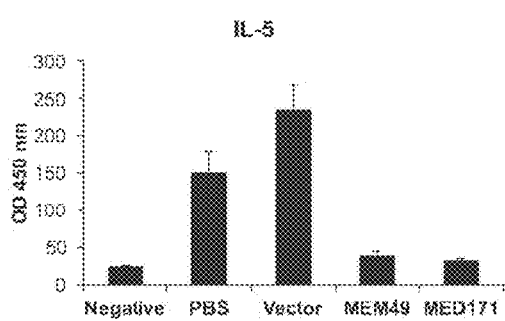
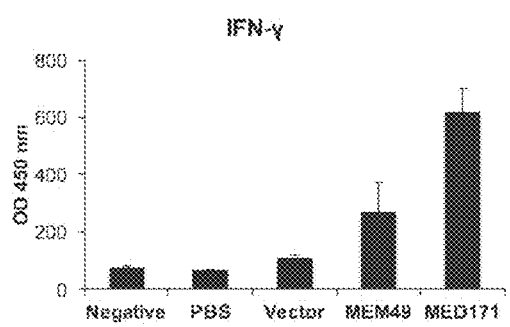
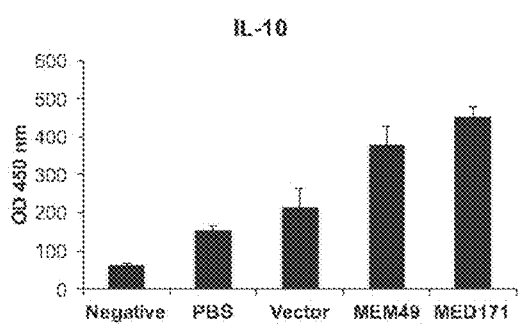
Fig. 12C
Fig. 12D

SEQUENCE LISTING

<160> NUMBER OF SEQ ID NOS: 10

<210> SEQ ID NO 1
<211> LENGTH: 822
<212> TYPE: DNA
<213> ORGANISM: Artificial Sequence
<220> FEATURE:
<223> OTHER INFORMATION: Synthetic construct

<400> SEQUENCE: 1

```
atgaaattag agaaagataa tgcgatggac cgcgctgata ccgctgaggg agacaaaaag      60
gaggccaata accgcgcaga gaagtctgaa gaagaattag tggcgctgca gaagaaattg     120
aaaggcaccg aagatgaact ggataagtat caggaaagcc tgctgaaggc taataatcag     180
ttagtggaga aggataaggc gctgagcaat gcggaaggcg aagtggcgag cctgaatcgt     240
cgtattcagc tggtcgagga agagctggat cgtgcacagg aacgcttaaa taccgcgacc     300
accaaactgg cggaagcgag ccaagcagca gacgagagcg agcgtatgcg taaagtgctt     360
gaaaaccgta gcctgagcga tgaagaacgt atggatgcgc tggaaattca gttaaaagaa     420
gcgaaacata ttgctgagga agcggatcgt aaatatgagg aggttgcgcg taaacttgct     480
atggtggaag cagatcttga acgggccgag gagcgtgctg aaaccgggga agcaaaatt     540
agcgagcttg aagaggagtt gaagaccgtg acgaacaatc tgaaaagtct ggaagcgcaa     600
gctgagaaag ctaaccagcg ggaggaggcg tataaagaac agattaaaac cctgaccaat     660
aaactgaaag cggcagaaac ccgtgcggaa tttgcggaac gtagcgtggc gaaactggaa     720
aagaccattg atgacctgga agacgaactg gtgaatgaaa aagagaaata caaagcgatt     780
tccgaagaac ttgatcatgc actgaatgat atgagcggct at                        822
```

<210> SEQ ID NO 2
<211> LENGTH: 513
<212> TYPE: DNA
<213> ORGANISM: Artificial Sequence
<220> FEATURE:
<223> OTHER INFORMATION: Synthetic construct

<400> SEQUENCE: 2

```
atgaagctgg agaaggataa cgccatggac agggcggata ccgaggccaa caacagggct    60
gagaagagcg aggaggagca ggaatccttg ctgaaggcaa acaaccagct cgtggagaag   120
gacaaggccc tctctaacgc tgagggtgag gttgctgaac gcctcaacac cgccaccacc   180
aagctggctg aggcctccca ggccgccgac gagtccgagc gcatgcgcaa ggtgctcgag   240
aaccgctccc tttccgatga ggagcgcatg gacgccctgg aggctgagga agccgacagg   300
gcccgtaagc tggccatggt tgaggccgac cttgagcgtg ctgaagaacg tgctgagact   360
ggtgaatcaa agatcgagaa ggctaaccaa cgcgaagagg cctacaagga gcagatcaag   420
accctgacca caagctgaa ggcggctttc gccgagaggt ctgtgctcga agacgaactg   480
gttaacgaaa aggagaagta caagtctggc tac                                513
```

<210> SEQ ID NO 3
<211> LENGTH: 274
<212> TYPE: PRT
<213> ORGANISM: Artificial Sequence
<220> FEATURE:
<223> OTHER INFORMATION: Synthetic construct

<400> SEQUENCE: 3

```
Met Lys Leu Glu Lys Asp Asn Ala Met Asp Arg Ala Asp Thr Ala Glu
1               5                   10                  15

Gly Asp Lys Lys Glu Ala Asn Asn Arg Ala Glu Lys Ser Glu Glu Glu
            20                  25                  30

Leu Val Ala Leu Gln Lys Lys Leu Lys Gly Thr Glu Asp Glu Leu Asp
        35                  40                  45

Lys Tyr Gln Glu Ser Leu Leu Lys Ala Asn Asn Gln Leu Val Glu Lys
    50                  55                  60

Asp Lys Ala Leu Ser Asn Ala Glu Gly Glu Val Ala Ser Leu Asn Arg
65                  70                  75                  80

Arg Ile Gln Leu Val Glu Glu Leu Asp Arg Ala Gln Glu Arg Leu
                85                  90                  95

Asn Thr Ala Thr Thr Lys Leu Ala Glu Ala Ser Gln Ala Ala Asp Glu
            100                 105                 110

Ser Glu Arg Met Arg Lys Val Leu Glu Asn Arg Ser Leu Ser Asp Glu
        115                 120                 125

Glu Arg Met Asp Ala Leu Glu Ile Gln Leu Lys Glu Ala Lys His Ile
    130                 135                 140

Ala Glu Glu Ala Asp Arg Lys Tyr Glu Glu Val Ala Arg Lys Leu Ala
145                 150                 155                 160

Met Val Glu Ala Asp Leu Glu Arg Ala Glu Arg Ala Glu Thr Gly
                165                 170                 175

Glu Ser Lys Ile Ser Glu Leu Glu Glu Glu Leu Lys Thr Val Thr Asn
            180                 185                 190

Asn Leu Lys Ser Leu Glu Ala Gln Ala Glu Lys Ala Asn Gln Arg Glu
        195                 200                 205

Glu Ala Tyr Lys Glu Gln Ile Lys Thr Leu Thr Asn Lys Leu Lys Ala
    210                 215                 220

Ala Glu Thr Arg Ala Glu Phe Ala Glu Arg Ser Val Ala Lys Leu Glu
225                 230                 235                 240

Lys Thr Ile Asp Asp Leu Glu Asp Glu Leu Val Asn Glu Lys Glu Lys
                245                 250                 255

Tyr Lys Ala Ile Ser Glu Glu Leu Asp His Ala Leu Asn Asp Met Ser
            260                 265                 270
```

Gly Tyr

<210> SEQ ID NO 4
<211> LENGTH: 171
<212> TYPE: PRT
<213> ORGANISM: Artificial Sequence
<220> FEATURE:
<223> OTHER INFORMATION: Synthetic construct

<400> SEQUENCE: 4

```
Met Lys Leu Glu Lys Asp Asn Ala Met Asp Arg Ala Asp Thr Glu Ala
1               5                   10                  15

Asn Asn Arg Ala Glu Lys Ser Glu Glu Gln Glu Ser Leu Leu Lys
            20                  25                  30

Ala Asn Asn Gln Leu Val Glu Lys Asp Lys Ala Leu Ser Asn Ala Glu
        35                  40                  45

Gly Glu Val Ala Glu Arg Leu Asn Thr Ala Thr Thr Lys Leu Ala Glu
    50                  55                  60

Ala Ser Gln Ala Ala Asp Glu Ser Glu Arg Met Arg Lys Val Leu Glu
65                  70                  75                  80

Asn Arg Ser Leu Ser Asp Glu Glu Arg Met Asp Ala Leu Glu Ala Glu
                85                  90                  95

Glu Ala Asp Arg Ala Arg Lys Leu Ala Met Val Glu Ala Asp Leu Glu
            100                 105                 110

Arg Ala Glu Glu Arg Ala Glu Thr Gly Glu Ser Lys Ile Glu Lys Ala
        115                 120                 125

Asn Gln Arg Glu Glu Ala Tyr Lys Glu Gln Ile Lys Thr Leu Thr Asn
    130                 135                 140

Lys Leu Lys Ala Ala Phe Ala Glu Arg Ser Val Leu Glu Asp Glu Leu
145                 150                 155                 160

Val Asn Glu Lys Glu Lys Tyr Lys Ser Gly Tyr
                165                 170
```

<210> SEQ ID NO 5
<211> LENGTH: 274
<212> TYPE: PRT
<213> ORGANISM: Metapenaeus ensis

<400> SEQUENCE: 5

```
Met Lys Leu Glu Lys Asp Asn Ala Met Asp Arg Ala Asp Thr Leu Glu
1               5                   10                  15

Gln Gln Asn Lys Glu Ala Asn Asn Arg Ala Glu Lys Ser Glu Glu Glu
            20                  25                  30

Val His Asn Leu Gln Lys Arg Met Gln Gln Leu Glu Asn Asp Leu Asp
        35                  40                  45

Gln Val Gln Glu Ser Leu Leu Lys Ala Asn Asn Gln Leu Val Glu Lys
    50                  55                  60

Asp Lys Ala Leu Ser Asn Ala Glu Gly Glu Val Ala Ala Leu Asn Arg
65                  70                  75                  80

Arg Ile Gln Leu Leu Glu Asp Leu Glu Arg Ser Glu Glu Arg Leu
                85                  90                  95

Asn Thr Ala Thr Thr Lys Leu Ala Glu Ala Ser Gln Ala Ala Asp Glu
            100                 105                 110

Ser Glu Arg Met Arg Lys Val Leu Glu Asn Arg Ser Leu Ser Asp Glu
        115                 120                 125

Glu Arg Met Asp Ala Leu Glu Asn Gln Leu Lys Glu Ala Arg Phe Leu
    130                 135                 140
```

Ala Glu Glu Ala Asp Arg Lys Tyr Asp Glu Val Ala Arg Lys Leu Ala
145                 150                 155                 160

Met Val Glu Ala Asp Leu Glu Arg Ala Glu Arg Ala Glu Thr Gly
            165                 170                 175

Glu Ser Lys Ile Val Glu Leu Glu Glu Glu Leu Arg Val Val Gly Asn
            180                 185                 190

Asn Leu Lys Ser Leu Glu Val Ser Glu Glu Lys Ala Asn Gln Arg Glu
            195                 200                 205

Glu Ala Tyr Lys Glu Gln Ile Lys Thr Leu Thr Asn Lys Leu Lys Ala
    210                 215                 220

Ala Glu Ala Arg Ala Glu Phe Ala Glu Arg Ser Val Gln Lys Leu Gln
225                 230                 235                 240

Lys Glu Val Asp Arg Leu Glu Asp Glu Leu Val Asn Glu Lys Glu Lys
                245                 250                 255

Tyr Lys Ser Ile Thr Asp Glu Leu Asp Gln Thr Phe Ser Glu Leu Ser
            260                 265                 270

Gly Tyr

<210> SEQ ID NO 6
<211> LENGTH: 23
<212> TYPE: DNA
<213> ORGANISM: Artificial Sequence
<220> FEATURE:
<223> OTHER INFORMATION: Synthetic construct

<400> SEQUENCE: 6
cgctcgagga tatcatgaaa tta                                           23

<210> SEQ ID NO 7
<211> LENGTH: 21
<212> TYPE: DNA
<213> ORGANISM: Artificial Sequence
<220> FEATURE:
<223> OTHER INFORMATION: Synthetic construct

<400> SEQUENCE: 7
cgtctagaaa gcttatagcc g                                             21

<210> SEQ ID NO 8
<211> LENGTH: 24
<212> TYPE: DNA
<213> ORGANISM: Artificial Sequence
<220> FEATURE:
<223> OTHER INFORMATION: Synthetic construct

<400> SEQUENCE: 8
cggaattcga tatcatgaag ctgg                                          24

<210> SEQ ID NO 9
<211> LENGTH: 21
<212> TYPE: DNA
<213> ORGANISM: Artificial Sequence
<220> FEATURE:
<223> OTHER INFORMATION: Synthetic construct

<400> SEQUENCE: 9
cgtctagaaa gcttgtagca g                                             21

<210> SEQ ID NO 10
<211> LENGTH: 22
<212> TYPE: DNA

```
<213> ORGANISM: Artificial Sequence
<220> FEATURE:
<223> OTHER INFORMATION: Synthetic construct

<400> SEQUENCE: 10
tgactgtgaa cgttcgagat ga                                              22
```

MET E 1 TROPOMYOSIN VARIANTS FOR USE IN ALLERGEN-SPECIFIC IMMUNOTHERAPY

RELATED APPLICATIONS

This application claims priority to U.S. Provisional Patent Application No. 62/241,476, filed Oct. 14, 2015, the contents of which are hereby incorporated by reference in the entirety for all purposes.

REFERENCE TO SUBMISSION OF A SEQUENCE LISTING AS A TEXT FILE

The Sequence Listing written in file 080015-017310US-1025331_SequenceListing.txt created on Dec. 9, 2016, 9803 bytes, machine format IBM-PC, MS-Windows operating system, is hereby incorporated by reference in its entirety for all purposes.

BACKGROUND OF THE INVENTION

Allergies to shellfish, e.g., shrimp, lobster, oysters, etc., are among the most common food allergies. The major allergen in shrimp is an invertebrate tropomyosin protein. At least 80% shrimp-allergic subjects react to tropomyosin, and the protein binds approximately 85% of the shrimp-specific IgE from shrimp-allergic subjects. Recent studies have shown that tropomyosin is a cross-reactive allergen and is found in other crustaceans such as lobster, crab, squid, snail and oyster, as well as other invertebrates, such as the house dust mite and cockroach (Ayuso et al., *Int Arch Allergy Immunol*, 2002, 129:38-48). A strong positive correlation has been established between IgE-mediated sensitization to shrimp, cockroach and dust mite (Wang et al., *J Allergy Clin Immunol*, 2011, 128(4):834-7; Shafique et al., *Allergy Rhinol*, 2012, 3:e74-e90).

After initial allergic sensitization (e.g., the initial exposure to the allergen and subsequent induction of allergen-specific IgE antibodies), an allergic reaction can arise upon exposure to the allergen. Cross-linking of the allergen specific-IgE antibodies bound to the surface of mast cells and basophils, degranulation of these cells, and release of inflammatory mediators, proteases, and pro-inflammatory cytokines lead to the symptoms associated with an allergic reaction.

Pharmaceutical treatment of allergy has focused on mitigation of allergic inflammation and often provides only temporary relief to the individual. Allergen-specific immunotherapy (SIT), on the other hand, is designed to provide long-last effects by modifying the individual's allergen-specific immune response. SIT is based on the repeated administration of a specific allergen to the individual over a period of time, e.g., years, such that the individual becomes desensitized to the allergen and can tolerate higher doses of the allergen without developing an allergic reaction. SIT involves the induction of antibodies against a specific allergen which block, and not enhance an allergic reaction.

There remains a need in the art for novel and efficacious prophylactic and treatment therapies for allergies to shellfish tropomyosins. The present invention satisfies this need and provides additional advantages as well.

BRIEF SUMMARY OF THE INVENTION

In one aspect, the present disclosure provides an isolated polypeptide comprising the amino acid sequence set forth in SEQ ID NO:3 or 4. The polypeptide can also include one or more heterologous amino acid sequences located at the N-terminus and/or the C-terminus of the polypeptide, such as one or more tag sequences that can facilitate isolation, identification, or detection of the polypeptide.

In another aspect, provided herein is an isolated nucleic acid comprising a polynucleotide sequence encoding the polypeptide described herein. The isolated nucleic acid can include the polynucleotide sequence set forth in SEQ ID NO:1 or 2.

In some aspects, provided herein is an expression cassette comprising the nucleic acid disclosed herein operably linked to a promoter, e.g., a heterologous promoter. In other aspects, provided herein is a vector comprising the nucleic acid or comprising the expression cassette. In yet other aspects, provided herein is a host cell that includes the nucleic acid or the expression cassette or the vector described herein.

In some aspects, the present disclosure provides a composition comprising the polypeptide or the nucleic acid described herein, and a physiologically acceptable excipient. The excipient can be an adjuvant. The compositions can be formulated for oral administration. Alternatively, the composition can be formulated for intradermal administration.

In certain aspects, provided herein is a method for reducing allergy in a subject, especially a human subject, comprising administering to the subject an effective amount of the polypeptide or the nucleic acid or the expression cassette or the vector described herein. Optionally, the administering step is repeated at least once, or twice or more, e.g., 2 times, 3 times, 4 times, 5 times, or more to the subject.

In some embodiments, the nucleic acid includes the polynucleotide sequence set forth in SEQ ID NO:1 or 2. The subject can be intradermally administered the nucleic acid or the expression cassette or the vector described above. Optionally, the nucleic acid or the expression cassette or the vector described above is administered in a composition comprising an adjuvant.

In some instances, the polypeptide administered to the subject includes the polypeptide sequence set forth in SEQ ID NO:3 or 4. In some embodiments, the subject is orally administered the polypeptide described above.

In some aspects, the present disclosure provides the use of the polypeptide or the nucleic acid or the expression cassette or the vector described herein for manufacturing a medicament for treating or preventing allergy.

In certain aspects, the present invention provides methods for inducing antibodies against an invertebrate tropomyosin protein, e.g., Met e 1 tropomyosin allergen, in a subject by administering a therapeutically effective amount of a nucleic acid encoding one or more Met e 1 polypeptide variants as described herein. In other aspects, the present invention provides methods for preventing, alleviating or modulating hypersensitivity (an allergic response) to an invertebrate tropomyosin protein, e.g., Met e 1 tropomyosin allergen, in a subject by administering a therapeutically effective amount of a nucleic acid encoding one or more one or more Met e 1 polypeptide variants as described herein. In yet other aspects, the present invention provides methods for developing or inducing tolerance or desensitization to an invertebrate tropomyosin protein e.g., Met e 1 tropomyosin allergen, in a subject by administering a therapeutically effective amount of a nucleic acid encoding one or more one or more Met e 1 polypeptide variants as described herein. In practicing the present invention, the subject receiving the treatment or being administered the compositions described herein may be any species of mammals, including primates such as humans.

Other objects, features, and advantages of the present invention will be apparent to one of skill in the art from the following detailed description and figures.

BRIEF DESCRIPTION OF THE DRAWINGS

FIG. 1 provides the polynucleotide sequence encoding a Met e 1 polypeptide variant containing 49 mutations in the IgE-binding epitopes (MEM49). The polynucleotide sequence of MEM49 is set forth in SEQ ID NO:1.

FIG. 2 provides the polynucleotide sequence encoding a Met e 1 polypeptide variant wherein the IgE-binding epitopes have been deleted (MED171). The polynucleotide sequence of MED171 is set forth in SEQ ID NO:2.

FIG. 3 illustrates an immunization schedule for a prophylactic treatment regimen. Mice were immunized intradermally with either a MEM49 vaccine or a MED171 vaccine. Afterwards, the mice were sensitized by subcutaneous injection of recombinant Met e 1 allergen (rMet e 1) and later, challenged with the recombinant Met e 1 allergen intragastrically to evaluate the prophylactic effects of the vaccine.

FIG. 4 illustrates an immunization schedule for a therapeutic regimen. Mice were intragastrically sensitized and challenged with recombinant Met e 1 allergen and then were treated with MEM49 or MED171 DNA vaccine. Afterwards, the mice were again challenged with recombinant Met e 1 allergen to evaluate the therapeutic effects of the MEM49 and MED171 DNA vaccines.

FIGS. 5A-5D show results of the prophylactic treatment experiment. After challenge with recombinant Met e 1 (rMet e 1), allergic responses were seen in mice in the PBS and vector control groups. Levels of mMCP-1 (FIG. 5A), mast cell infiltration (FIG. 5B), eosinophil infiltration (FIG. 5C), and goblet cell hyperplasia (FIG. 5D) in the jejunum were higher in the groups treated with PBS or the vector control compared to those receiving the MEM49 vaccine or MED171 vaccine.

FIGS. 6A-6D show serological analysis of mice in the prophylactic treatment experiment. Levels of Met e 1-specific IgE (FIG. 6A), Met e 1-specific IgG1 (FIG. 6B), Met e 1-specific IgG2a (FIG. 6C), and Met e 1-specific IgG2b (FIG. 6D) were measured after rMet e 1 sensitization and challenge.

FIGS. 7A-7C show the levels of Met e 1-recognizing IgG antibodies that were induced upon MEM49 immunization or MED171 immunization, and rMet e 1 challenge. Levels of Met e 1-specific IgG1 (FIG. 7A), Met e 1-specific IgG2a (FIG. 7B), and Met e 1-specific IgG2b (FIG. 7C) are shown.

FIGS. 8A-8D show the induction of blocking IgG antibodies upon DNA immunization with MEM49 and MED171 and rMet e 1 allergen challenge. FIG. 8A provides results from a competitive inhibition ELISA. Post-vaccination sera from the MEM49-vaccinated group inhibited the binding of mouse IgE to rMet e 1. FIG. 8B shows after rMet e 1 challenge, sera from MEM49- and MED171-vaccinated mice blocked the binding of mouse IgE to the rMet e 1 allergen. FIG. 8C shows that sera from MEM49- and MED171-vaccinated mice after rMet e 1 challenge inhibited the binding of human IgE from human subjects with a shrimp allergy (A94, A167, A205, A230, A237, A244, A264, A290 and A399) to rMet e 1. FIG. 8D shows data from a passive cutaneous anaphylaxis assay.

FIGS. 9A-9D show levels of IL-5 (FIG. 9A), IFN-γ (FIG. 9B), IL-12 (p40) (FIG. 9C) and IL-10 (FIG. 9D) in in vitro splenocyte cultures derived from mice in the prophylactic treatment experiment.

FIG. 10A-L provides the expression levels of genes in the small intestine of mice in the prophylactic experiment. The data show expression of IL-4 (FIG. 10A), IL-5 (FIG. 10B), IL-13 (FIG. 10C), IL-12 (FIG. 10D), IFN-γ (FIG. 10E), IL-18 (FIG. 10F), IL-10 (FIG. 10G), FOXP3 (FIG. 10H), TGF-β (FIG. 10I), CD25 (FIG. 10J), RUNX1 (FIG. 10K) and RUNX3 (FIG. 10L).

FIG. 11 shows the therapeutic effects of MEM49- and MED171-encoding DNA vaccines on mice of the therapeutic treatment experiment. The data illustrate reduction in IgE synthesis.

FIGS. 12A-D shows levels of Th1, Th2 and Treg-associated cytokines in splenocytes isolated from all groups of mice after the second recombinant Met e 1 allergen challenge. The data show levels of IL-4 (FIG. 12A), IL-5 (FIG. 12B), IFN-γ (FIG. 12C) and IL-10 (FIG. 12D).

FIGS. 13A-D provides the expression levels of genes in the small intestine of mice in the therapeutic treatment experiment. The data show expression levels of IFN-γ (FIG. 13A), IL-10 (FIG. 13B), TGF-β (FIG. 13C) and FOXP3 (FIG. 13D).

DETAILED DESCRIPTION OF THE INVENTION

I. Introduction

Provided herein are immunoprophylatic and/or immunotherapeutic therapies that target shellfish allergy. The therapies include Met e 1 tropomyosin hypoallergens and hypoallergen-encoding DNA vaccines. The Met e 1 hypoallergens described herein have low to no IgE reactivity and allergenicity. As such, they are a safer alternative to the use of allergen extracts or recombinant allergens to treat allergy.

II. Definitions

As used herein, the following terms have the meanings ascribed to them unless specified otherwise.

The terms “a,” “an,” or “the” as used herein not only include aspects with one member, but also include aspects with more than one member. For instance, the singular forms “a,” “an,” and “the” include plural referents unless the context clearly dictates otherwise. Thus, for example, reference to “a cell” includes a plurality of such cells and reference to “the agent” includes reference to one or more agents known to those skilled in the art, and so forth.

The terms “about” and “approximately” shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms “about” and “approximately” may mean values that are within an order of magnitude, preferably within 5-fold and more preferably within 2-fold of a given value. Numerical quantities given herein are approximate unless stated otherwise, meaning that the term “about” or “approximately” can be inferred when not expressly stated.

The term “Met e 1” refers to a *Metapenaeus ensis* (shrimp) tropomyosin allergen. Serum antibodies from patients with a shrimp allergy may exhibit positive IgE reactivity by, for example, immunoblotting to a Met e 1 tropomyosin protein. The *Metapenaeus ensis* tropomyosin (Met e 1) polypeptide sequence is set forth in, e.g., UniProt No. Q25456 and EMBL Accession No. AAA60330. The *Metapenaeus ensis* tropomyosin (Met e 1) mRNA (coding) sequence is set forth in, e.g., EMBL Accession No. U08008.

Figure 3:
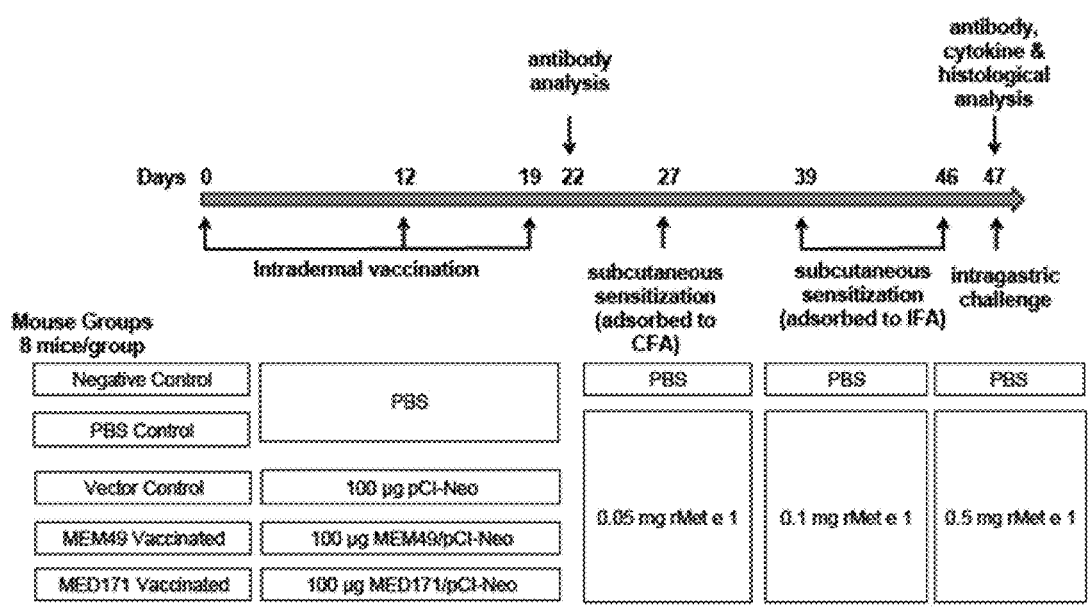

The term "peptide," "polypeptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including peptides (i.e., epitopes), wherein the amino acid residues are linked by covalent peptide bonds.

The term "amino acid" includes naturally-occurring α-amino acids and their stereoisomers, as well as unnatural (non-naturally occurring) amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an α carbon that is bound to a hydrogen, a carboxyl group, an amino group, but have modified R (i.e., side-chain) groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The term "amino acid modification" or "amino acid alteration" refers to a substitution, a deletion, or an insertion of one or more amino acids.

The term "nucleic acid," "nucleotide" or "polynucleotide" refers to deoxyribonucleic acids (DNA) or ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), orthologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991), Ohtsuka et al., *J. Biol. Chem.* 260:2605-2608 (1985), and Rossolini et al., *Mol. Cell. Probes* 8:91-98 (1994)). The term nucleic acid is used interchangeably with gene, cDNA, and mRNA encoded by a gene.

The term "nucleotide sequence encoding a peptide" or "gene" means the segment of DNA involved in producing a peptide chain, it includes regions preceding and following the coding region (leader and trailer) involved in the transcription/translation of the gene product and the regulation of the transcription/translation, as well as intervening sequences (introns) between individual coding segments (exons). The leader, the trailer as well as the introns include regulatory elements that are necessary during the transcription and the translation of a gene (e.g., promoters, terminators, translational regulatory sequences such as ribosome binding sites and internal ribosome entry sites, enhancers, silencers, insulators, boundary elements, replication origins, matrix attachment sites and locus control regions, etc.). A "gene product" can refer to either the mRNA or protein expressed from a particular gene.

"Percentage of sequence identity" is determined by comparing two optimally aligned sequences over a comparison window, wherein the portion of the sequence (e.g., a peptide of the invention) in the comparison window may comprise additions or deletions (i.e., gaps) as compared to the reference sequence which does not comprise additions or deletions, for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity.

The term "percent identity" or "percent sequence identity," in the context of describing two or more polynucleotide or amino acid sequences, refer to two or more sequences or subsequences that are the same or have a specified percentage of amino acid residues or nucleotides that are the same (for example, a variant of a peptide of interest used in the method of this invention has at least 80% sequence identity, preferably 85%, 90%, 91%, 92%, 93, 94%, 95%, 96%, 97%, 98%, 99%, or 100% identity, to a reference sequence, e.g., a corresponding epitope or antigen, when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 8 amino acids in length, or more preferably over a region that is at least 8-25 or at least 8 to 12 amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Additional examples of algorithms that are suitable for determining percent sequence identity and sequence similarity are the BLAST and BLAST 2.0 algorithms, which are described in Altschul et al., (1990) *J Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see, e.g., Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA,* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or peptides are substantially identical is that the peptide encoded by the first nucleic acid is immunologically cross reactive with the antibodies raised against the peptide encoded by the second nucleic acid. Thus, a peptide is typically substantially identical to a second peptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The terms "transfection" or "transfected" refer to introduction of a nucleic acid into a cell by non-viral or viral-based methods. The nucleic acid molecules may be gene sequences encoding complete proteins or functional portions thereof. See, e.g., Sambrook et al., 1989, Molecular Cloning: A Laboratory Manual, 18.1-18.88.

The term "expression" or "expressed" in the context of a gene refers to the transcriptional and/or translational product of the gene. The level of expression of a DNA molecule in a cell may be determined on the basis of either the amount of corresponding mRNA that is present within the cell or the amount of protein encoded by that DNA produced by the cell.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The term "promoter," as used herein, refers to a polynucleotide sequence capable of driving transcription of a coding sequence in a cell. Thus, promoters used in the polynucleotide constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "constitutive promoter" is one that is capable of initiating transcription in nearly all tissue types, whereas a "tissue-specific promoter" initiates transcription only in one or a few particular tissue types. An "inducible promoter" is one that initiates transcription only under particular environmental conditions or developmental conditions.

A polynucleotide/polypeptide sequence is "heterologous" to an organism or a second polynucleotide/polypeptide sequence if it originates from a different species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, e.g., from a different gene in the same species, or an allele from a different ecotype or variety).

Nucleic acid or amino acid sequences are "operably linked" (or "operatively linked") when placed into a functional relationship with one another. For instance, a promoter or enhancer is operably linked to a coding sequence if it regulates, or contributes to the modulation of, the transcription of the coding sequence. Operably linked DNA sequences are typically contiguous, and operably linked amino acid sequences are typically contiguous and in the same reading frame. However, since enhancers generally function when separated from the promoter by up to several kilobases or more and intronic sequences may be of variable lengths, some polynucleotide elements may be operably linked but not contiguous. Similarly, certain amino acid sequences that are non-contiguous in a primary polypeptide sequence may nonetheless be operably linked due to, for example folding of a polypeptide chain.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. For example, recombinant cells express genes that are not found within the native (non-recombinant) form of the cell or express native genes that are otherwise abnormally expressed, under-expressed, or not expressed at all.

An "expression cassette" refers to a nucleic acid construct, which when introduced into a host cell, results in transcription and/or translation of a RNA or polypeptide, respectively. Antisense constructs or sense constructs that are not or cannot be translated are expressly included by this definition. One of skill will recognize that the inserted polynucleotide sequence need not be identical, but may be only substantially similar to a sequence of the gene from which it was derived.

The term "vector" or "recombinant expression vector" refers a nucleic acid construct, generated recombinantly or synthetically, with a series of specified nucleic acid elements that permit transcription of a particular polynucleotide sequence in a host cell. An expression vector may be part of a plasmid, viral genome, or nucleic acid fragment. Typically, an expression vector includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence.

The term "promoter" is used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Other elements that may be present in an expression vector include those that enhance transcription (e.g., enhancers) and terminate transcription (e.g., terminators), as well as those that confer certain binding affinity or antigenicity to the recombinant peptide or protein produced from the expression vector.

The term "allergen" refers not only to naturally occurring allergen extracts and allergen molecules but also to mutants of allergens, hypoallergens or parts of allergen molecules, such as polypeptides. Allergens are able to trigger an allergy, that is, an immediate-type hypersensitivity reaction, which is induced by the synthesis of IgE antibodies. Hypoallergens are natural or recombinant derivatives of an allergen molecule which, due to slight differences compared with the amino acid sequence of the allergen, assume a conformation by which IgE-binding properties are lost.

The term "epitope" refers to a binding site including an amino acid motif (e.g., a linear amino acid sequence or a particular three dimensional structure) which can be bound by an immunoglobulin (e.g., IgE, IgG, etc.) or recognized by a T-cell receptor when presented by an APC in conjunction within the major histocompatibility complex (MHC). Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solve s. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics such as a mixture of cells or a cell lysate. Thus, under designated immunoassay conditions, the specified antibodies bind to a particular protein (at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Using Antibodies, A Laboratory Manual* (1998) for a description of immunoassay formats and conditions that can be used to determine specific immunoreactivity).

The term "shellfish" refers to aquatic invertebrates with an exoskeleton that are consumed by humans. The term shellfish includes members of the phylum Arthropoda, class or subphylum Crustacea, such as shrimp, prawns, crab, lobster, crawfish, and barnacles; the phylum Mollusca, such as oysters, mussels, scallops, clams, geoducks, abalone, whelk, conch, squid, octopus, cuttlefish, and nautilus; and the phylum Echinodermata, such as sea urchins, starfish, and sea cucumbers.

The phrase "inducing antibodies against a tropomyosin protein" refers to generating or producing antibodies that specifically bind to a tropomyosin protein (anti-tropomyosin antibodies). In some embodiments of allergen immunotherapy or hyposensitization, antibodies such as IgG and/or IgA class are generated/produced by the subject and can block the binding of allergen-specific IgE antibodies (e.g., anti-tropomyosin IgE antibodies) to the allergen (e.g., the allergenic tropomyosin protein) in the subject.

The "allergic reaction" or "allergic response" refers to an immune response that is IgE mediated with clinical symptoms primarily involving the cutaneous (e.g., uticana, angiodema, pruritus), respiratory (e.g., wheezing, coughing, laryngeal edema, rhinorrhea, watery/itching eyes), gastrointestinal (e.g., vomiting, abdominal pain, diarrhea) cardiovascular (i.e., if a systemic reaction occurs) systems, and any combination thereof.

The phrase "preventing, alleviating, or modulating hypersensitivity to" an allergen refers to reducing, decreasing, minimizing or eliminating an allergic response to a specific allergen upon exposure to the allergen, or providing preexposure prophylaxis to prevent an IgE-mediated allergic reaction (e.g., a hypersensitivity reaction). In some cases, the phrase includes inducing hyposensitivity or desensitization to the allergen.

The phrase "developing tolerance to a tropomyosin protein" refers to developing immunity or immune tolerance for an allergenic tropomyosin protein in a subject, which may reduce the risk of having an allergic reaction to the tropomyosin allergen.

The terms "treat," "treating" and "treatment" refer to the administering of a therapeutically effective anti-inflammatory amount of the peptide, nucleic acid, or a pharmaceutical composition comprising same which is effective to ameliorate undesired symptoms associated with inflammation, to prevent the manifestation of such symptoms before they occur, to slow down the progression of an inflammatory condition, to slow down the deterioration of symptoms associated with an inflammatory condition, to slow down the irreversible damage caused by the chronic stage of an inflammatory condition, to lessen the severity or cure an inflammatory condition, to improve survival rate or more rapid recovery form such a condition. It should be noted that in the context of the present invention the term "treatment" also denotes "prophylactic treatment", i.e. for prevention of the development of an inflammatory condition or to prevent the re-occurrence of an acute inflammatory phase in a chronic individual. To this end, the molecule may be administered to individuals who do not have inflammation and especially, to individuals having a high-risk of developing an inflammatory condition, e.g. as a result of exposure to an infecting agent or allergen. In this case, the molecule will typically be administered over an extended period of time in a single daily dose (e.g. to produce a cumulative effective amount), in several doses a day, as a single dose for several days, etc. so as to prevent the manifestation of inflammation.

The term "administering" or "administration" of a therapeutic peptide, nucleic acid or composition to a subject includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, epicutaneous, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of a peptide of the invention for preventing or relieving one or more symptoms associated with the presence or activity of maternal antibodies. By "co-administer" it is meant that a peptide of the invention is administered at the same time, just prior to, or just after the administration of a second drug.

The term "physiologically acceptable excipient" or "pharmaceutically acceptable carrier" refers to a substance that aids the administration of an active agent to a cell, an organism, or a subject. "Physiologically acceptable excipient" refers to a carrier or excipient that can be included in the compositions of the invention and that causes no significant adverse toxicological effect on the patient. Non-limiting examples of pharmaceutically acceptable carrier include water, NaCl, normal saline solutions, lactated Ringer's, normal sucrose, normal glucose, binders, fillers, disintegrants, lubricants, coatings, sweeteners, flavors and colors, liposomes, dispersion media, microcapsules, cationic lipid carriers, isotonic and absorption delaying agents, and the like. The excipient may also be substances for providing the formulation with stability, sterility and isotonicity (e.g. antimicrobial preservatives, antioxidants, chelating agents and buffers), for preventing the action of microorganisms (e.g. antimicrobial and antifungal agents, such as parabens, chlorobutanol, phenol, sorbic acid and the like) or for providing the formulation with an edible flavor etc. In some instances, the carrier is an agent that facilitates the delivery of the amino acid molecule to a target cell or tissue. One of skill in the art will recognize that other physiologically acceptable excipient are useful in the present invention.

The term "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). The therapeutically effective amount may vary depending upon one or more of: the subject and disease condition being treated, the weight and age of the subject, the severity of the disease condition, the manner of administration and the like, which can readily be determined by one of ordinary skill in the art. The specific amount may vary depending on one or more of: the particular agent chosen, the target cell type, the location of the target cell in the subject, the dosing regimen to be followed, whether it is administered in combination with other compounds, timing of administration, and the physical delivery system in which it is carried.

For the purposes herein an effective amount is determined by such considerations as may be known in the art. The amount must be effective to achieve the desired anti-inflammatory effect in a subject suffering from an inflammatory state, the desired anti-inflammatory effect include, for example, amelioration of undesired symptoms associated with inflammation, prevention of the manifestation of such symptoms before they occur, slowing down progression of an inflammatory condition, slowing down the deterioration of symptoms associated with an inflammatory condition, slowing down any irreversible damage caused by a chronic stage of an inflammatory condition, lessening of the severity or curing an inflammatory condition, improving survival rate or providing more rapid recovery form such a condition. Further, in the context of prophylactic treatment the amount may also be effective to prevent the development of an inflammatory condition.

The effective amount depends, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the molecule to the corresponding receptor, its distribution profile within the body, a variety of pharmacological parameters such as half-life in the body, on undesired side effects, if any, on factors such as age and gender, etc.

The term "adjuvant" refers to a compound or mixture that enhances the immune response to an antigen. An adjuvant can serve as a depot that slowly releases the antigen and also as a lymphoid system activator that non-specifically enhances the immune response (Hood et al., Immunology, Second Ed., 1984, Benjamin/Cummings: Menlo Park, Calif., p. 384) Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, dinitrophenol, and potentially useful human adjuvants such as BCG (bacille Calmette-Guerin) and *Corynebacterium parvum*. Typically, the adjuvant is pharmaceutically acceptable. In some instances, the adjuvant or carrier can be a serum albumin.

III. Detailed Description of the Embodiments

A. Isolated Met e 1 Polypeptide Variants

The present disclosure provides an isolated Met e 1 polypeptide having at least about 80%, e.g., at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to any one of the amino acid sequences set forth in SEQ ID NO:3 or 4. In some embodiments, the polypeptide comprises an amino acid sequence comprising or consisting of any one of the sequences as set forth in SEQ ID NO: 3 or 4. In other embodiments, the isolated peptide has 100% sequence identity to any one of the amino acid sequences set forth in SEQ ID NO:3 or 4.

In some embodiments, the isolated polypeptide includes conserved amino acid substitutions, insertions and/or deletions. The polypeptide can also include one or more heterologous amino acid sequences located at the N-terminus and/or the C-terminus of the polypeptide.

The polypeptide when used for immunotherapy can induce antibodies, including blocking antibodies against a tropomyosin allergen, e.g., Met e 1 allergen. In some cases, the polypeptide can induce the production of antibodies that recognize one or more tropomyosin proteins or one or more tropomyosin epitopes. For example, a polypeptide provided herein can be used to generate antibodies in a subject that specifically bind to a tropomyosin protein of, for example, shrimp.

In some embodiments, the polypeptide includes variants that are further modified to improve their resistance to proteolytic degradation or to optimize solubility properties or to render them more suitable as a therapeutic agent. For example, the polypeptide further includes analogs containing residues other than naturally occurring L-amino acids, e.g., D-amino acids or non-naturally occurring synthetic amino acids. D-amino acids may be substituted for some or all of the amino acid residues.

In certain embodiments, the polypeptide comprises naturally-occurring amino acids and/or unnatural amino acids. Examples of unnatural amino acids include, but are not limited to, D-amino acids, ornithine, diaminobutyric acid ornithine, norleucine ornithine, pyriylalanine, thienylalanine, naphthylalanine, phenylglycine, alpha and alpha-disubstituted amino acids, N-alkyl amino acids, lactic acid, halide derivatives of naturally-occurring amino acids (e.g., trifluorotyrosine, p-Cl-phenylalanine, p-Br-phenylalanine, p-I-phenylalanine, etc.), L-allyl-glycine, b-alanine, L-a- amino butyric acid, L-g-amino butyric acid, L-a-amino isobutyric acid, L-e-amino caproic acid, 7-amino heptanoic acid, L methionine sulfone, L-norleucine, L-norvaline, p-nitro-L-phenylalanine, L-hydroxyproline, L-thioproline, methyl derivatives of phenylalanine (e.g., 1-methyl-Phe, pentamethyl-Phe, L-Phe (4-amino), L-Tyr (methyl), L-Phe (4-isopropyl), L-Tic (1,2,3,4-tetrahydroisoquinoline-3-carboxyl acid), L-diaminopropionic acid, L-Phe (4-benzyl), etc.). The polypeptide may be further modified. For example, one or more amide bonds may be replaced by ester or alkyl backbone bonds. There may be N- or C-alkyl substituents, side-chain modifications, or constraints such as disulfide bridges or side-chain amide or ester linkages.

In some embodiments, the polypeptide includes both modified peptides and synthetic peptide analogues. Polypeptides may be modified to improve formulation and storage properties, or to protect labile peptide bonds by incorporating non-peptidic structures.

The polypeptides of the present invention can be produced by any suitable means known or later discovered in the field, e.g., synthesized in vitro, purified or substantially purified from a natural source, recombinantly produced from eukaryotic or prokaryotic cells, etc.

The peptides may be prepared by in vitro synthesis, using conventional methods as known in the art. For example, polypeptides may be produced by chemical synthesis, e.g., using solid phase techniques and/or automated peptide synthesizers. In certain instances, polypeptides may be synthesized using solid phase strategies on an automated multiple peptide synthesizer (Abimed AMS 422) using 9-fluorenylmethyloxycarbonyl (Fmoc) chemistry. The polypeptides can then be purified by reversed phase-HPLC and lyophilized. By using synthesizers, naturally-occurring amino acids may be substituted with unnatural amino acids. The particular sequence and the manner of preparation will be determined by convenience, economics, purity required, and the like. The polypeptides may alternatively be prepared by cleavage of a full-length protein sequence.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. Methods which are well known to those skilled in the art can be used to construct expression vectors containing coding sequences and appropriate transcriptional/translational control signals. These methods include, for example, in vitro recombinant DNA techniques, synthetic techniques, and in vivo recombination/genetic recombination. See, e.g., Sambrook and Russell, Molecular Cloning: A Laboratory Manual, 3rd Ed., 2001, Cold Spring Harbor Laboratory Press; and Ausubel, et al., Current Protocols in Molecular Biology, 1987-2009, John Wiley Interscience.

In some embodiments, the polynucleotide sequence encoding the polypeptide is altered to coincide with the preferred codon usage of a particular host cell. For example, the preferred codon usage of one strain of bacterial cells can be used to derive a polynucleotide that encodes a recombinant polypeptide of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). One of skill in the art can readily utilize well-known codon usage tables and synthetic methods to provide a suitable coding sequence for any of the peptides of the invention.

Once the recombinant polypeptide is expressed in the host cell, the polypeptide can be purified according to standard known to those in the art. Methods of lysing the host cells and isolating a recombinant polypeptide are described in, for example, Ausubel et al. and Sambrook et al., both supra.

B. Isolated Nucleic Acids Encoding Met e 1 Polypeptide Variants

The present disclosure provides an isolated nucleic acid that encodes an isolated peptide described above. In some embodiments, provided herein is an isolated nucleic acid having at least about 80%, e.g., at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to either of the sequences set forth in SEQ ID NO:1 or 2. In some embodiments, the isolated nucleic acid provided herein has 100% sequence identity to either of the sequences set forth in SEQ ID NO:1 or 2.

In some embodiments, provided herein is an isolated nucleic acid that encodes a polypeptide having at least about 80%, e.g., at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to any one of the sequences set forth in SEQ ID NO: 3 or 4. In some embodiments, the isolated nucleic acid provided herein encodes a polypeptide having 100% sequence identity to any one of sequences set forth in SEQ ID NO: 3 or 4.

The disclosure also provides a vector comprising an isolated nucleic acid provided herein, an expression cassette comprising an isolated nucleic acid provided herein operably linked to a promoter, a host cell comprising the vector or expression cassette, and a polypeptide encoded by a nucleic acid. The expression cassette or vector can include the polypeptide-encoding nucleic acid operably linked to suitable transcriptional and/or translational regulatory elements (e.g., a sequence to control expression) to effect expression in a suitable host cell. The regulatory elements may be derived from mammalian, microbial, viral or insect genes, and include, for example, promoters, enhancers, transcription and translation initiation sequences, termination sequences, origins of replication, and sequences encoding leader and transport sequences. Suitable regulatory elements are selected for optimal expression in a desired host cell. Useful expression vectors can be constructed by methods known to one of ordinary skill in the art, and are also commercially available. Exemplary recombinant viral vectors, include retrovirus, parvovirus, densovirus and baculovirus vectors.

The expression cassette or vector can include a strong constitutive or inducible promoter operatively linked to a nucleic acid of the disclosure. Suitable promoters are well known and readily available to one of ordinary skill in the art and include, for example, bacterial, yeast, viral, mammalian, and insect promoters. Exemplary expression vectors are vectors compatible with mammalian cells.

The host cell can include an expression cassette or a vector or an isolated nucleic acid as described herein. The host cell may be prokaryotic or eukaryotic, including bacterial, yeast, insect or mammalian cells. In some cases, the host cell can be a plant cell. In some embodiments, the host cells are insect or mammalian cells. The isolated nucleic acids or vectors, e.g., expression vectors, may be introduced into the host cells by methods known to one of ordinary skill in the art, including transformation, transfection and infection. For example, transfection may be accomplished by any known method, such as liposome-mediated transfection, calcium phosphate-mediated transfection, naked DNA transfection, microinjection or electroporation. Transformation methods suitable for prokaryotic cells are described, for example, in Cohen et al., Proc. Natl. Acad. Sci. (USA) 69:2110 (1972). Transformation of eukaryotic host cells is described, for example, in Sambrook et al., supra. The host cells containing the isolated nucleic acid or vectors are useful for replicating the vector and expressing the nucleic acid encoding the peptide of interest, or for replicating and expressing the isolated nucleic acid.

Viral vector systems useful in the expression of the nucleic acid include, but are not limited to, naturally-occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, the nucleic acid of interest is inserted into such vectors to allow packaging of the construct, typically with accompanying viral DNA, followed by infection of a sensitive host cell and expression of the nucleic acid of interest.

Viral envelopes used for packaging gene constructs that include the nucleic acid can be modified by the addition of receptor ligands or antibodies specific for a receptor to permit receptor-mediated endocytosis into specific cells (see, e.g., PCT Publication Nos. WO 93/20221, WO 93/14188, and WO 94/06923). In some embodiments, the DNA constructs are linked to viral proteins, such as adenovirus particles, to facilitate endocytosis (Curiel et al., Proc. Natl. Acad. Sci. U.S.A., 88:8850-8854 (1991)).

Retroviral vectors are also useful for introducing the nucleic acid into target cells or organisms. Retroviral vectors are produced by genetically manipulating retroviruses. The viral genome of retroviruses is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild-type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: *Experimental Manipulation of Gene Expression*, Inouye (ed), 155-173 (1983); Mann et al., *Cell* 33:153-159 (1983); Cone and Mulligan, *Proceedings of the National Academy of Sciences, U.S.A.*, 81:6349-6353 (1984)).

The design of retroviral vectors is well known to those of ordinary skill in the art. In brief, if the sequences necessary for encapsidation (or packaging of retroviral RNA into infectious virions) are missing from the viral genome, the result is a cis-acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent No. 0178220; U.S. Pat. No. 4,405,712; Gilboa, *Biotechniques*, 4:504-512 (1986); Mann et al., *Cell*, 33:153-159 (1983); Cone and Mulligan, *Proc. Natl. Acad. Sci. USA*, 81:6349-6353 (1984); Eglitis et al., *Biotechniques* 6:608-614 (1988); Miller et al., *Biotechniques*, 7:981-990 (1989); and PCT Publication No. WO 92/07943.

The retroviral vector particles are prepared by recombinantly inserting the desired polynucleotide sequence into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired polynucleotide sequence. As a result, the individual is capable of producing, for example, a polypeptide of interest.

Packaging cell lines that are used to prepare the retroviral vector particles are typically recombinant mammalian tissue culture cell lines that produce the necessary viral structural proteins required for packaging, but which are incapable of producing infectious virions. The defective retroviral vectors that are used, on the other hand, lack these structural genes but encode the remaining proteins necessary for packaging. To prepare a packaging cell line, one can construct an infectious clone of a desired retrovirus in which the packaging site has been deleted. Cells comprising this construct will express all structural viral proteins, but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available. Examples of these cell lines include Crip, GPE86, PA317 and PG13 (see Miller et al., *J. Virol.*, 65:2220-2224 (1991)). Examples of other packaging cell lines are described in Cone and Mulligan. *Proc. Natl. Acad. Sci. USA*, 81:6349-6353 (1984); Danos and Mulligan. *Proc. Natl. Acad. Sci. USA*, 85:6460-6464 (1988); Eglitis et al. (1988), supra; and Miller (1989), supra.

Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

C. Pharmaceutical Compositions

The polypeptide or nucleic acid encoding the polypeptide described herein can be formulated for immunotherapy. In some embodiments, the composition includes any one of the isolated polypeptides described herein. In other embodiments, the compositions include two or more of any of the polypeptides provided herein.

Useful methods for formulating polypeptides for immunotherapy are known to those of ordinary skill in the art. For example, U.S. Patent Publication No. 2003/0049237 discloses methods of encapsulating antigens to reduce association of antigen with antigen-specific IgE antibodies, thereby reducing the risk of allergic reaction and, possibly, anaphylactic shock. It also discloses methods of modifying IgE binding sites of allergens to reduce allergenicity, for example by masking the IgE binding site or altering an amino acid within the protein. International Patent Publication No. WO 00/74716 discloses various carriers for peptides, as well as peptide-based vaccines in the absence of protein carriers, and compositions comprising a plurality of allergy peptides linked by an inert carrier.

The pharmaceutical compositions of the invention may comprise a pharmaceutically acceptable carrier. In certain aspects, pharmaceutically acceptable carriers are determined in part by the particular composition being administered, as well as by the particular method used to administer the composition. Accordingly, there is a wide variety of suitable formulations of pharmaceutical compositions of the present invention (see, e.g., REMINGTON'S PHARMACEUTICAL SCIENCES, 18TH ED., Mack Publishing Co., Easton, Pa. (1990)). Formulations for use in accordance with the disclosure must be stable under the conditions of manufacture and storage and must also be preserved against the contaminating action of microorganisms such as bacteria and fungi. Prevention against microorganism contamination can be achieved through the addition of one or more of various antibacterial and antifungal agents.

The pharmaceutical forms suitable for administration include sterile aqueous solutions or dispersions and sterile powders for the extemporaneous preparation of sterile injectable solutions or dispersions. In all cases, the form must be sterile and must be fluid to the extent that suitable syringability exists. Typical carriers include a solvent or dispersion medium containing, for example, water-buffered aqueous solutions (i.e., biocompatible buffers), ethanol, polyols such as glycerol, propylene glycol, polyethylene glycol, suitable mixtures thereof, surfactants, or vegetable oils.

Sterilization can be accomplished by an art-recognized technique, including but not limited to filtration or addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing a polypeptide (s), nucleic acid(s) and/or composition(s) is accomplished by incorporating the compound(s) in the required amount(s) in the appropriate solvent with various ingredients enumerated above, as required, followed by sterilization, preferably filter sterilization. To obtain a sterile powder, the above sterile solutions are vacuum-dried or freeze-dried as necessary.

In the practice of this invention, the compositions can be administered, for example, intravenously, intracranially, intrathecally, intraspinally, intraperitoneally, intradermally, intramuscularly, intralesionally, intranasally, subcutaneously, intracerebroventricularly, intralymphatically, orally, topically, sublingually, epicutaneously and/or by inhalation.

For systemic administration, injection may be used e.g. intradermal, subcutaneous, intramuscular, intravenous, etc. For injection, the compositions described herein can be formulated in liquid solutions, such as in physiologically compatible buffers such as Hank's solution or Ringer's solution. Alternatively, the compositions are formulated in one or more excipients (e.g., propylene glycol) that are generally accepted as safe as defined by USP standards. They can, for example, be suspended in an inert oil, suitably a vegetable oil such as sesame, peanut, olive oil, or other acceptable carrier.

In some embodiments, the compositions are suspended in an aqueous carrier, for example, in an isotonic buffer solution at pH of about 5.6 to 7.4. These compositions can be sterilized by conventional sterilization techniques, or can be sterile filtered. The compositions can contain pharmaceutically acceptable auxiliary substances as required to approximate physiological conditions, such as pH buffering agents. Useful buffers include for example, sodium acetate/acetic acid buffers. A form of repository or "depot" slow release preparation can be used so that therapeutically effective amounts of the preparation are delivered into the bloodstream over many hours or days following transdermal injection or delivery. In addition, the compounds can be formulated in solid form and redissolved or suspended immediately prior to use. Lyophilized forms are also included.

In some embodiments, the polypeptide(s), nucleic acid(s) and/or composition(s) provided herein are formulated for administration, e.g., oral, nasal, topical, or parental administration in unit dosage form for ease of administration and uniformity of dosage. Unit dosage forms, as used herein, refers to physically discrete units suited as unitary dosages for the subjects, e.g., humans or other mammals to be treated, each unit containing a predetermined quantity of active material calculated to produce the desired therapeutic effect in association with the required pharmaceutical carrier. In some instances, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the polypeptide(s), nucleic acid(s) and/or composition(s).

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In certain embodiments, the dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" refers to physically discrete units suitable as unitary dosages for humans and other mammals, each unit containing a predetermined quantity of an imaging agent or therapeutic agent calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the imaging agent or therapeutic agent.

Methods for preparing such dosage forms are known to those skilled in the art (see, e.g., REMINGTON'S PHARMACEUTICAL SCIENCES, supra). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like. Additional components of the formulation include a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. In some embodiments, a suitable carrier masks the composition, e.g., the polypeptide or nucleic acid from the mouth and upper gastrointestinal (GI) tract and reduce or prevent local itching/swelling reactions in these regions during administration. For example, a carrier may contain one or more lipid, polysaccharide or protein constituents. In some cases, the carrier is a food product.

Liquid dosage forms can be prepared by dissolving or dispersing a therapeutic agent and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration.

For topical administration, the therapeutically effective dose can be in the form of emulsions, lotions, gels, foams, creams, jellies, solutions, suspensions, ointments, and transdermal patches. For administration by inhalation, an imaging agent or therapeutic agent can be delivered as a dry powder or in liquid form via a nebulizer. Aerosol formulations can be placed into pressurized acceptable propellants such as dichlorodifluoromethane. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

In some embodiments, the therapeutically effective dose may further comprise other components, for example, anti-allergy drugs, such as antihistamines, steroids, bronchodilators, leukotriene stabilizers and mast cell stabilizers. Suitable anti-allergy drugs are well known in the art. This may be useful in reducing allergic inflammation and increasing tolerance of a tropomyosin allergen.

D. Methods of Administration

In the methods of administration as described herein, the polypeptides, nucleic acids, or compositions may be administered in a manner compatible with the dosage formulation, in such amount as will be therapeutically effective, and in any way that is medically acceptable for the treatment of the specific allergy. Possible administration routes include oral, nasal, transdermal, topical, and parenteral administration such as intralymphatic, intravascular, intravenous, intra-arterial, epicutaneous, subcutaneous, intramuscular, intradermal, intraperitoneal, intraventricular or intraepidural. Examples of oral administration include buccal, sublabial, and sublingual administration. In some cases, administration is by inhalation. In some cases, sustained release administration is also used.

The polypeptides, nucleic acids, or compositions provided herein can be used to generate antibodies in, for example, a subject with an allergy to shellfish. The method for treating an allergy to shellfish in a subject in need thereof include administering an effective amount of one or more polypeptides, one or more nucleic acids, and/or one or more compositions described herein. A therapeutically effective amount of the polypeptide(s), nucleic acid(s) and/or composition(s) represents an amount effective to achieve hyposensitization to a specific allergen. The precise therapeutically effective amount of the polypeptide(s), nucleic acid(s) and/or composition(s) can be determined by the ordinary skilled artisan with consideration of individual differences in age, weight, extent of disease and condition of the patient.

E. DNA-Based Vaccines

For an antigenic composition to be useful as a vaccine, the antigenic composition must induce an immune response to the antigen in a cell, tissue or mammal (e.g., a human). Preferably, the vaccine induces a protective immune response in the mammal. As used herein, a "composition" may comprise, by way of examples, an antigen (e.g., a polypeptide), a nucleic acid encoding an antigen (e.g., expression cassette or vector), or a cell expressing or presenting an antigen. In particular embodiments the composition comprises or encodes all or part of any polypeptide described herein, or an immunologically functional equivalent thereof. In some instances, the composition contains a nucleic acid encodes all or part of any polypeptide described herein. Such compositions are useful as DNA based vaccines to prevent and/or treat, for example, an allergy. Detailed descriptions of DNA based vaccines can be found in, e.g., Kutzler and Weiner, *Nat Rev Genetics*, 2008, 9: 776-788.

The nucleic acid based composition, e.g., a nucleic acid encoding a Met e 1 variant described herein, an expression cassette containing the nucleic acid operably linked to a promoter and a vector containing the nucleic acid, may be naked, in that, it is not associated with any proteins or other agents that may impact the subject's immune system. The naked DNA may be in a physiologically acceptable solution, such as, but not limited to, sterile saline or sterile buffered saline. In other embodiments, the composition is in a mixture that includes a nucleic acid encoding a Met e 1 variant and an additional physiologically acceptable excipient such as an adjuvant. Optionally, an immunostimulatory agent can include but is not limited to, a polypeptide, a nucleic acid, or an immunomodulator.

In some embodiments, the composition includes any polypeptide disclosed herein or any nucleic acid disclosed herein, in combination with an adjuvant. Alternatively, the composition can include one or more adjuvants. Non-limiting examples of an adjuvant include, Freund's incomplete adjuvant, immune-stimulating complexes (ISCOMS), an LPS analog including monophosphoryl lipid A, muramyl peptides, quinone analogs and vesicles such as squalene and squalene, and hyaluronic acid. Additional components of a vaccine include a lipid or liposome, calcium ions, viral proteins, polyanions, polycations, or nanoparticles, or other known transfection facilitating agents.

In some embodiments, the nucleic composition also includes an immunostimulatory agent. Such an immunostimulatory agent can be an oligonucleotide such as an immunostimulatory sequence oligodeozynucleotides (ISS-ODN). A non-limiting example of an ISS-ODN includes 5'-TGACTGTGAACGTTCGAGATGA-'3 (SEQ ID NO:10). Optionally, the composition can also include a Met e 1 polypeptide described herein.

The composition containing a nucleic acid encoding a Met e 1 variant or an expression cassette thereof or a vector thereof as described herein can be used as a DNA-based vaccine to treat shellfish allergy. In some embodiments, the composition is administered at a dosage of about 0.01 μg-1000 μg or more, e.g., 0.01 μg, 0.1 μg, 1 μg, 10 μg, 20 μg, 30 μg, 40 μg, 50 μg, 60 μg, 70 μg, 80 μg, 90 μg, 100 μg, 200 μg, 300 μg, 400 μg, 500 μg, 600 μg, 700 μg, 800 μg, 900 μg, 1000 μg or more. In other embodiments, the composition is administered to a subject at a dosage ranging from about 0.01 μg-100 μg, e.g., 0.01 μg, 0.1 μg, 0.5 μg, 1 μg, 5 μg, 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, or 100 μg. In other embodiments, the dosage administered to the subject is about 0.01 μg-100 μg, e.g., about 0.01 μg-100 μg, 0.1 μg-100 μg, 1 μg-100 μg, 10 μg-100 μg, 20 μg-100 μg, 50 μg-100 μg, 0.01 μg-50 μg, 0.1 μg-50 μg, 1 μg-50 μg, 10 μg-50 μg, 20 μg-50 μg, and the like.

The composition may be formulated to have a nucleic acid concentration of 0.1 mg/ml or more, e.g., 0.1 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml or more. In some embodiments, the composition comprises about 1 ng to 100 mg of nucleic acid, e.g., 1 ng to 100 mg, 1 μg to 100 mg, 1 mg to 100 mg, 1 ng to 1 mg, 1 ng to 1 mg, 1 ng to 1 μg, 1 μg to 10 mg or 1 mg to 10 mg of nucleic acid. The composition can contain about 1 ng to 100 mg of nucleic acid, e.g., 1 ng, 10 ng, 100 ng, 1 μg 10 μg, 100 μg, 1 mg, 10 mg, or 100 mg of nucleic acid.

The nucleic acid based composition can be delivered intradermal injection, intramuscular injection, intramuscular injection followed by electroporation, or orally. Examples of electroporation devices and electroporation methods for facilitating delivery of the DNA based vaccines include those described in U.S. Pat. No. 7,245,963 and U.S. Patent Pub. No. 2005/0052630, the disclosures of which are hereby incorporated by reference in their entirety for all purposes.

In some cases, the subject is given repetitive immunizations of the composition. The nucleic acid based composition can be administered weekly, once every two weeks, once every three weeks, once a month, or once a year. In some cases, the composition is administered once a week for 3 to 4 weeks, then once a month for 3 additional months. Other schedules are possible such that more or less frequent immunizations can be administered over longer periods of time. In some embodiments, the composition is administered to the subject according to an immunization schedule that is useful for treating an allergy and/or preventing an allergic response.

In some embodiments, the first administration of a DNA-based vaccine is given without a pharmaceutically acceptable carrier, and subsequent doses are administered with an adjuvant. In some cases, the subject is administered a homologous prime-boost vaccination such that the same composition is given in the priming immunizations and the subsequent boost immunizations. Alternatively, the subject can be administered a heterologous prime-boost vaccination such that a composition is given in the priming immunization and a different composition is given at the subsequence boost immunizations. For example, the nucleic acid composition described herein can be administered at the priming immunization and the polypeptide composition described herein is given in the boost immunizations.

IV. Examples

The following examples are provided by way of illustration only and not by way of limitation. Those of skill in the art will readily recognize a variety of non-critical parameters that could be changed or modified to yield essentially the same or similar results.

Example 1

Met e 1 Hypoallergen-Encoding DNA Vaccines for Shellfish Allergy

There is currently no allergen-specific immunotherapy (SIT) targeting at shellfish allergy. As the use of unmodified allergens in conventional SIT often triggers allergic side effects, hypoallergens with low/no allergenicity are ideal alternatives. Moreover, the use of Th1-promoting DNA plasmids as carrier is shown to be effective in the prevention and/or treatment of allergy, a Th2 immune response-dominated disorder. Based on these hypotheses, the present invention describes two hypoallergen-encoding DNA vaccines specific for tropomyosin-induced shellfish allergy, as well as their prophylactic and therapeutic applications targeting at tropomyosin-induced shellfish allergy. With their high safety profile and efficacies, the invention described herein can be applied clinically for immunoprophylactic and/or immunotherapeutic uses for shellfish allergy.

Methods

Construction of Hypoallergen-encoding Vaccines

Coding sequences of MEM49 (FIG. 1) and MED171 (FIG. 2) were cloned into mammalian expression vector pCI-Neo using standard molecular methods. MEM49 was inserted via XhoI/XbaI restriction sites using forward primer 5'-CGCTCGAGGATATCATGAAATTA-3' (SEQ ID NO: 6) and reverse primer 5'-CGTCTAGAAAGCTTATAGCCG-3' (SEQ ID NO: 7). MED171 was inserted via EcoRI/XbaI restriction sites using forward primer 5'-CGGAATTCGATATCATGAAGCTGG-3' (SEQ ID NO: 8) and reverse primer 5'-CGTCTAGAAAGCTTGTAGCAG-3' (SEQ ID NO: 9). Encoding sequences in the plasmids were confirmed by dideoxynucleotide sequencing. The resulting vectors, designated as MEM49/pCI-Neo and MED171/pCI-Neo, were cultured in *Escherichia coli* DH5α and purified using the Plasmid Maxi Kit. Concentration of the purified plasmids was determined by nano-drop.

Prophylactic and Therapeutic Regimen Designs

In the prophylactic treatment regimen, mice in the MEM49 and MED171-vaccinated groups were immunized intradermally with 100 μg of MEM49/pCI-Neo and MED171/pCI-Neo, respectively, on days 0, 12 and 19 (FIG. 3). Mice in the PBS and vector control groups were given PBS and naked pCI-Neo, respectively. One week after, all mice except those in the negative control group were sensitized by means of subcutaneous injection of rMet e 1 adsorbed to Freund's complete and incomplete adjuvants. These mice were finally challenged with 0.5 mg rMet e 1 intragastrically to evaluate the prophylactic effects of the vaccine.

Figure 4:
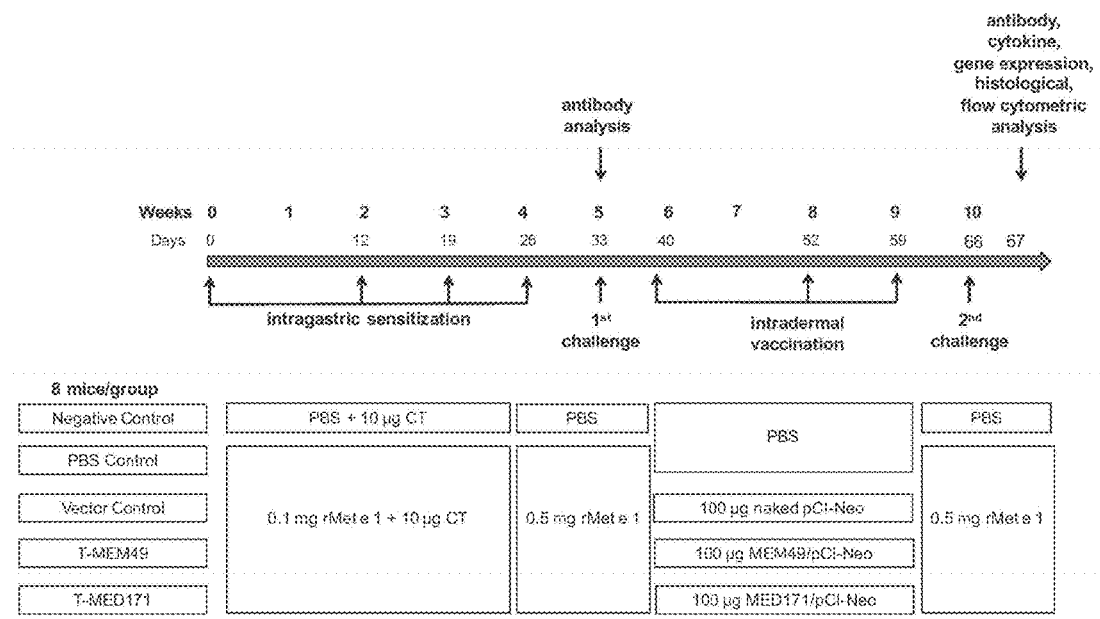

In the therapeutic regimen, mice in all groups except those in the negative control group were intragastrically sensitized and challenged with rMet e 1 on days 0, 12, 19, 26 and 33 (FIG. 4). One week after, mice in the MEM49 and MED171 treatment groups were then intradermally treated with 100 μg of MEM49/pCI-Neo or MED171/pCI-Neo, respectively, on days 40, 52 and 59. Mice in the PBS control group were given equal volume of PBS as sham treatment while mice in the vector control group were given 100 μg of naked pCI-Neo. On day 66, these mice received a second 0.5 mg rMet e 1 challenge to evaluate the therapeutic effects of the vaccine. Mice in the negative control were given PBS throughout the experiment.

Results

Figure 5A:
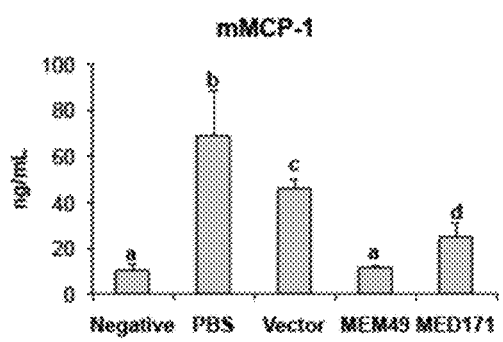
Figure 5B:
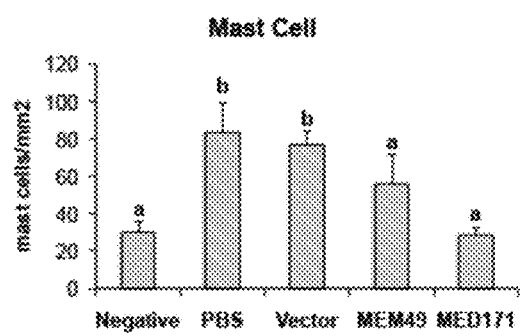
Figure 5C:
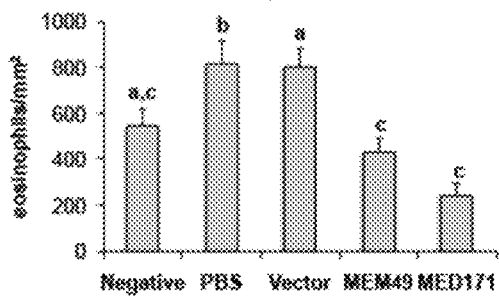
Figure 5D:
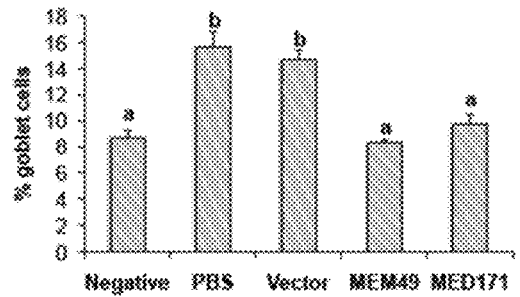

Prophylactic Effects of the Hypoallergen-encoding DNA Vaccines (1) Prevention of the Onset of Shrimp Allergy Mice in the PBS and vector control groups developed allergic responses upon rMet e 1 challenge, including high levels of mMCP-1 and significant inflammatory responses in the jejunum (i.e., mast cell and eosinophil infiltration, as well as goblet cell hyperplasia) (FIGS. 5A-5D). Serological analysis also revealed high levels of rMet e 1-specific IgE in these groups of mice (FIG. 6A). On the contrary, MEM49- and MED171-vaccinated mice only displayed basal levels of mMCP-1 and specific IgE (FIGS. 5A and 6A). Mast cell and eosinophil infiltration, as well as goblet cell hyperplasia could not be observed in the jejunum in these vaccinated mice (FIGS. 5B and 5C), indicating the prevention of shrimp allergy development upon hypoallergen-encoding DNA vaccine immunization.

(2) Induction of Blocking IgG Antibodies

Met e 1-recognizing IgG antibodies were induced upon MEM49/pCI-Neo or MED171/pCI-Neo immunization (FIGS. 7A-7C), suggesting that these DNA vaccines were capable of inducing strong humoral responses alone. Three subclasses of IgG antibodies, IgG1, IgG2a and IgG2b could be detected at high levels among the MEM49-vaccinated mice. However, only specific IgG1 antibodies were induced upon MED171/pCI-Neo immunization. After Met e 1 sensitization and challenge, specific IgG1 antibodies were detected at high levels in all groups of sensitized mice (FIG. 6B). Although both IgG2a and IgG2b antibodies could be found in the sera of PBS and vector control mice, levels of these antibodies were significantly higher among the vaccinated mice (FIGS. 6C and 6D).

Figure 8A:
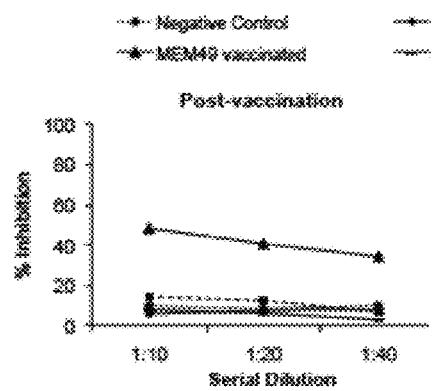
Figure 8B:
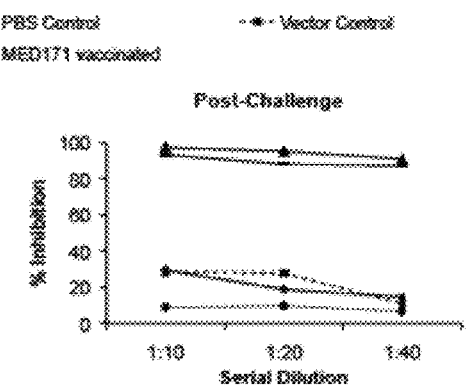
Figure 8C:
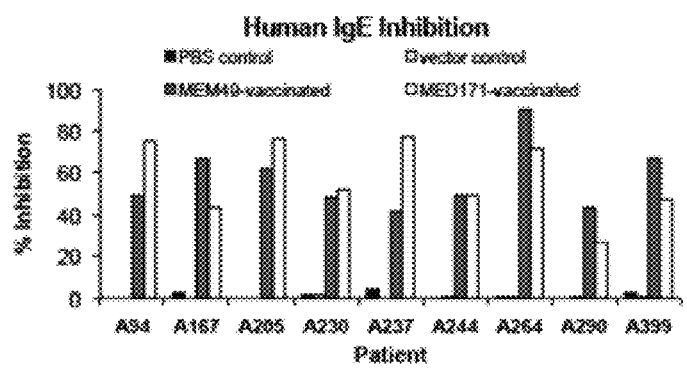

IgG2a antibodies are generally regarded as blocking antibodies. We therefore investigated if the IgG2a antibodies induced upon DNA immunization and Met e 1 challenge could play an inhibitory role. By means of competitive inhibition ELISA, post-vaccination sera from the MEM49-vaccinated group could block 48% mouse IgE from binding to rMet e 1 at 1:10 dilution (FIG. 8A). Blocking was not significant in the MED171-vaccinated group even with the presence of IgG1. After Met e 1 challenge, sera from MEM49- and MED171-vaccinated groups could inhibit 97% and 93% mouse IgE from binding to Met e 1, as well as 57.6±5.0% and 57.7±5.7% IgE of shrimp allergy subjects from binding to Met e 1, respectively (FIGS. 8B and 8C). Notably, an approximately 30% inhibition to mouse IgE and no significant inhibition to human IgE were exhibited by sera from PBS and vector control groups.

Figure 8D:
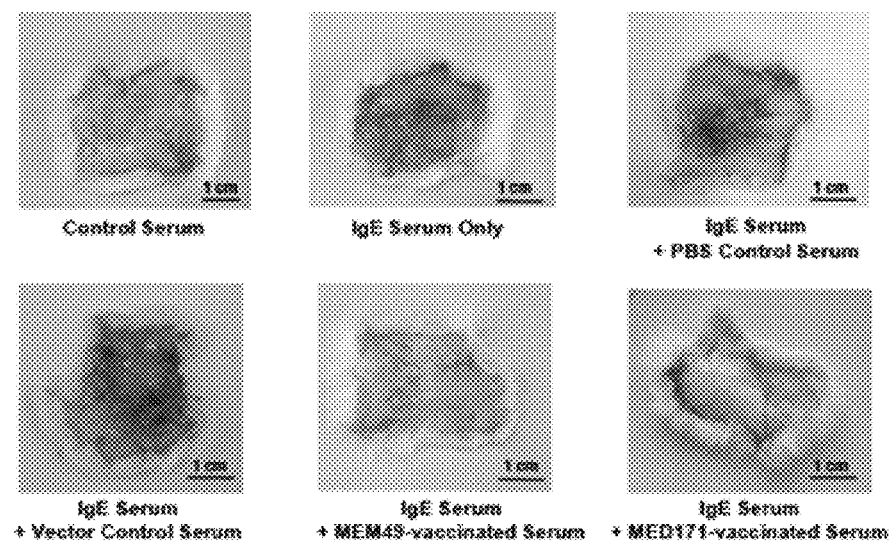
Figure 9A:
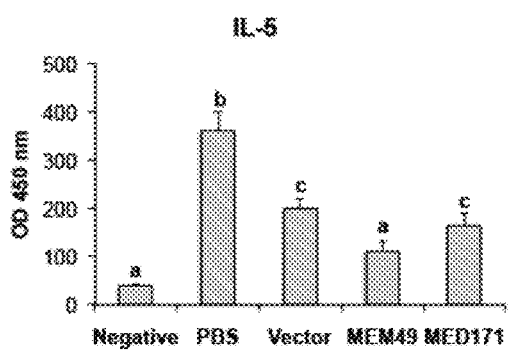
Figure 9B:
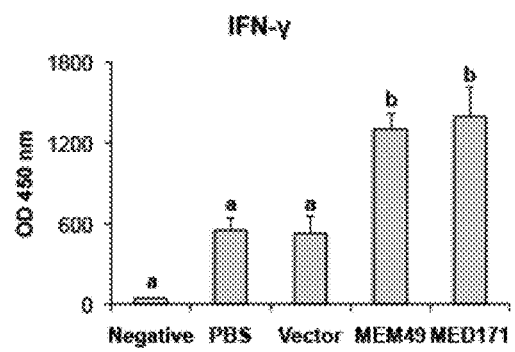
Figure 9C:
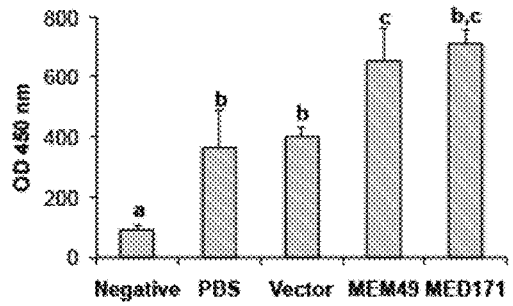
Figure 9D:
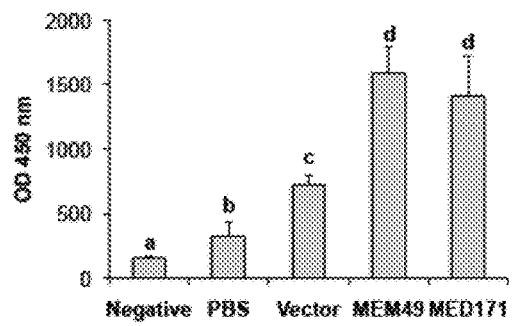

In vivo inhibitory potential of the post-challenge sera was further investigated by passive cutaneous anaphylaxis assay (PCA). The binding of IgE antibodies and the specific allergen on mast cells could induce mast cell degranulation and cause rapid histamine and serotinin release. This leads to local increase in vessel permeability and extravasation of Evan's blue dye into the surrounding tissues. Therefore, dyed regions of >2 cm diameters could be observed at the back skin on naïve mice upon the injection of IgE serum, co-injection of IgE serum and sera from PBS or vector control groups (FIG. 8D). However, with the presence of sera from MEM49- or MED171-vaccinated mice, no Evan's blue dye extravasation could be observed. This suggests that the IgG antibodies in the vaccinated sera are able to block IgE from binding to mast cells and inhibit the subsequent degranulation responses.

(3) Induction of Th1 responses and recruitment of regulatory T cells

Analysis of in vitro splenocyte culture by ELISA (FIGS. 9A-9D) and gene expression at ileum by real-time PCR (FIGS. 10A-10L) revealed a low level and expression of IL-4, IL-5 and IL-13 among the MEM49-vaccinated mice (FIGS. 9A, 10A, 10B and 10C), thus further confirming the full-bodied protection against shrimp allergy upon MEM49/pCI-Neo vaccination. Although expression of IL-4 remained basal, protection against shrimp allergy by MED171/pCI-Neo was less robust as the level and expression of IL-5 and IL-13 were comparable to the PBS and vector control groups.

Figure 10A:
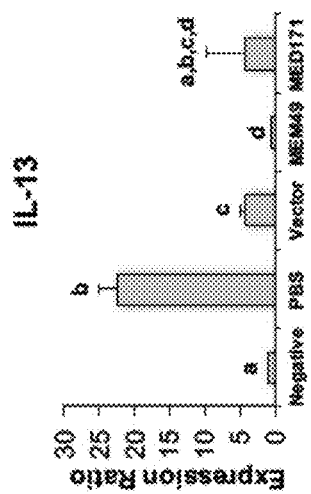
Figure 10B:
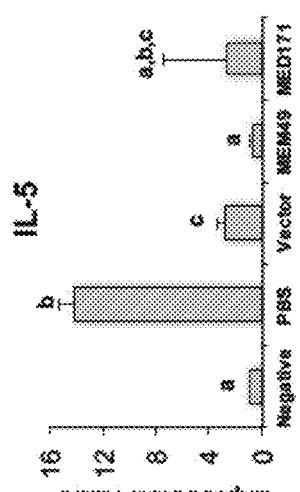
Figure 10C:
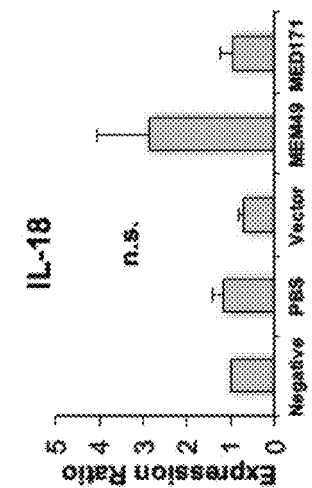
Figure 10D:
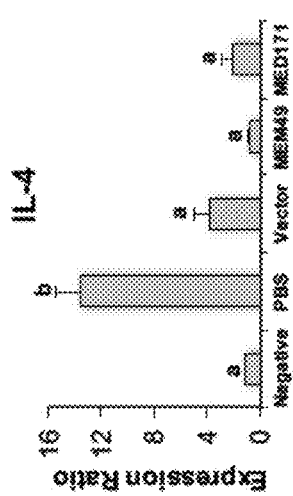
Figure 10E:
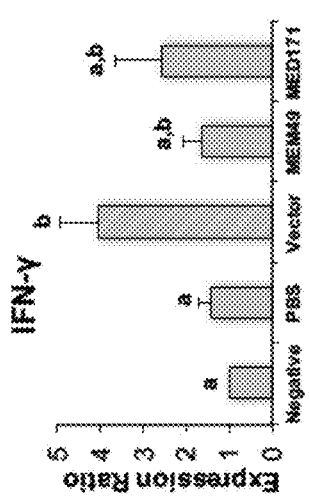
Figure 10F:
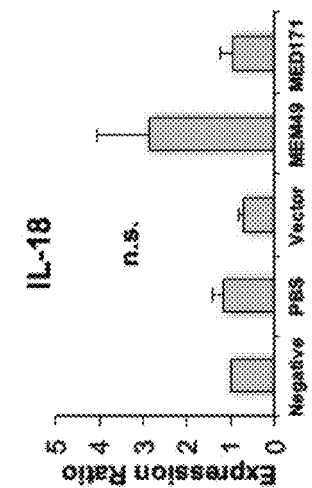
Figure 10G:
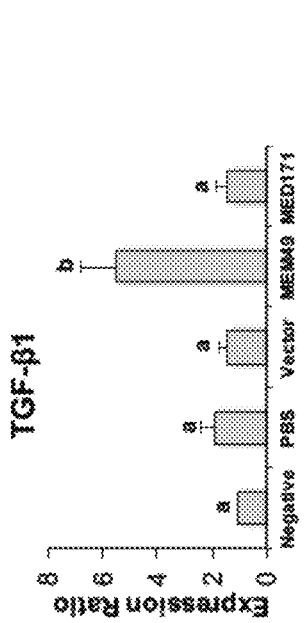
Figure 10H:
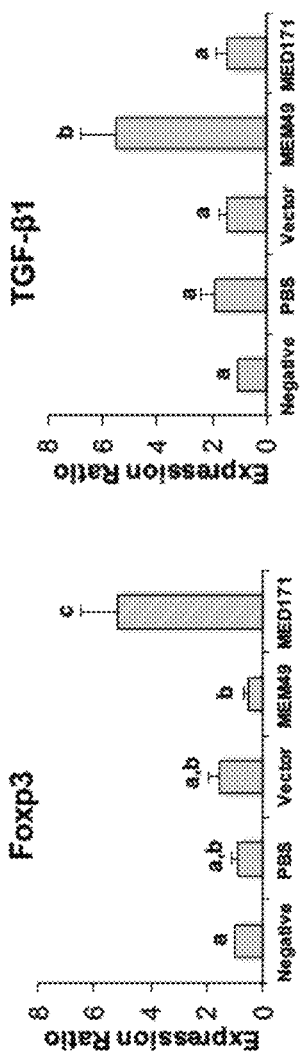
Figure 10I:
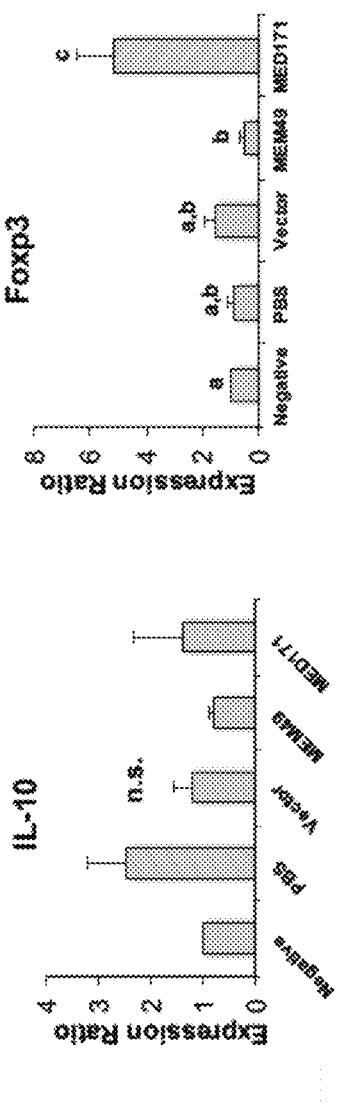
Figure 10J:
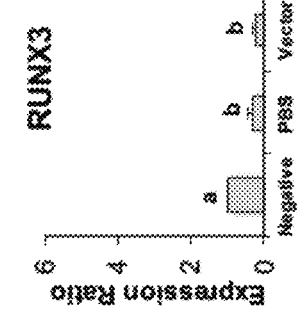
Figure 10K:
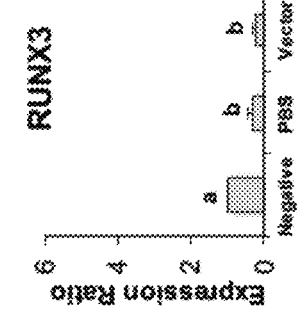
Figure 10L:

Notably, significantly higher levels of splenic IFN-γ and IL-12 (Th1 cytokines) and IL-10 (Treg cytokine) (FIGS. 9B, 9C and 9D), and over-expression of Foxp3, CD25 and RUNX3 (Treg-associated genes) at the ileum (FIGS. 10H, 10J and 10L) could be detected among the MED171-vaccinated mice. The presence of these counteracting Th1 and Treg responses might explain the absence of inflammatory responses among the MED171-vaccinated mice. Interestingly, although the splenic cytokine responses were similar between the two groups of vaccinated mice, RT-PCR analysis revealed the over-expression of TGF-β and CD25 (Treg-associated genes) among the MEM49-vaccinated mice (FIGS. 10I and 10J). These suggest different pathways generated by MEM49- and MED171-encoding DNA vaccines in the prevention of shrimp allergy, which warrant further mechanistic investigations.

Figure 11:
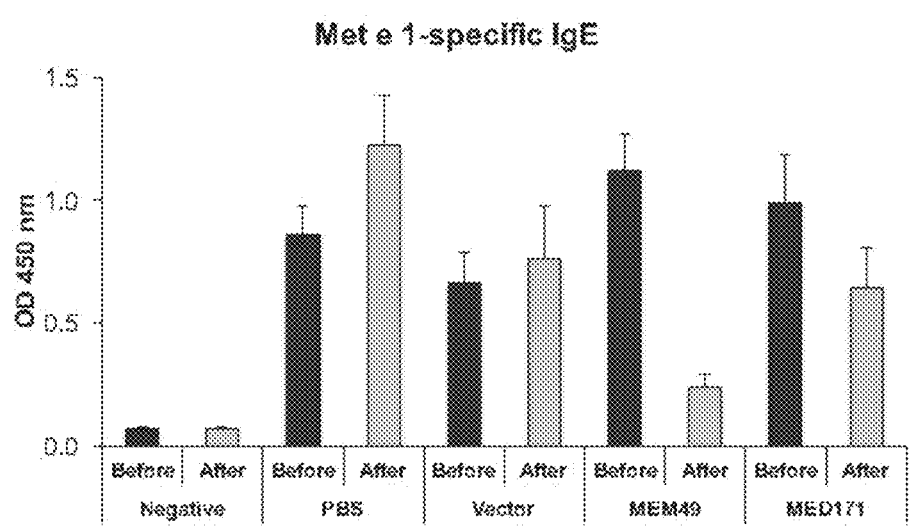

Therapeutic Effects of Hypoallergen-encoding DNA Vaccines (1) Reduction of IgE Synthesis and Th2 Responses To investigate the therapeutic effects of the two hypoallergen-encoding DNA vaccines, mice with tropomyosin-induced allergy were intradermally injected with the vaccine thrice. For the sham-treated mice (i.e. treated with PBS or naked plasmid), their level of Met e 1-specific IgE remained high upon first (before treatment) and second (after treatment) rMet e 1 challenge (FIG. 11). On the contrary, mice that were treated with MEM49/pCI-Neo or MED171/pCI-Neo had their level of Met e 1-specific IgE dropped by 76% and 69%, respectively. On the other hand, to evaluate the cytokine responses upon vaccine treatment, all groups of mice were sacrificed after the second rMet e 1 challenge. Individual spleens were then isolated as single cell suspension and stimulated with rMet e 1. Splenocytes from mice in the PBS and vector control groups synthesized high levels of IL-4 and IL-5 (FIGS. 12A, B). On the contrary, spleen cells from mice received MEM49/pCI-Neo or MED171/pCI-Neo treatment produced low levels of IL-4 and IL-5. These indicated that both hypoallergen-encoding DNA vaccines are capable of ameliorating the already-established Th2 allergic responses in mice.

(2) Induction of Th1 and Treg Responses

Figure 13A:
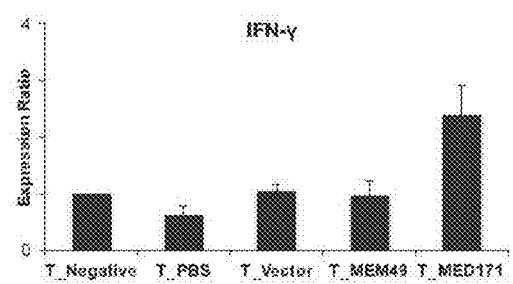
Figure 13B:
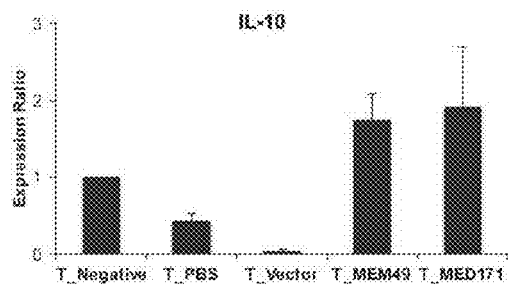
Figure 13C:
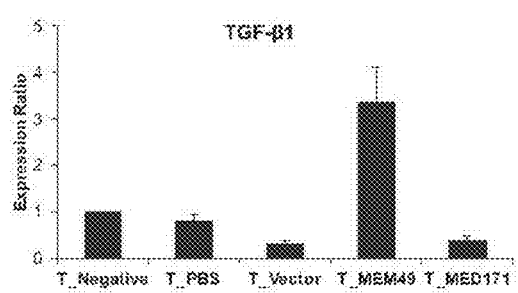
Figure 13D:
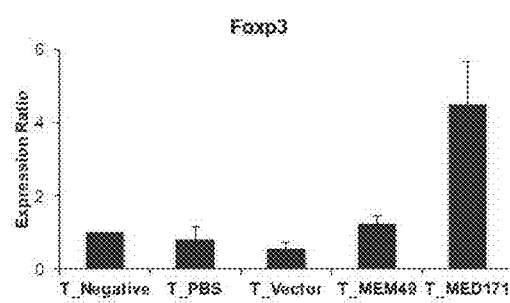

In contrast to the low levels of IFN-γ and IL-10 secreted from splenocytes of PBS and vector control mice, high levels of these cytokines were detected in mice received MEM49/pCI-Neo or MED171/pCI-Neo treatment (FIGS. 12C, D). Such induction of Th1 and Treg responses could also be detected in the small intestine of treated mice. IFN-γ expression was found higher in mice received MED171/pCI-Neo treatment (FIG. 13A). Despite the upregulation of IL-10 expression in mice treated with either of the DNA vaccines, only TGF-β and Foxp3 were found un-regulated in mice received MEM49/pCI-Neo and MED171/pCI-Neo treatments, respectively (FIGS. 13B, C, D). This highlighted the different modulatory mechanisms driven by the two DNA vaccines.

In summary, the data show that both MEM49- and MED171-encoding DNA vaccines are capable of reducing shrimp allergy reactions and level of tropomyosin-specific IgE through promoting Th1 and Treg responses. The MEM49-encoding DNA vaccine and MED171-encoding DNA vaccine described herein can both be used as vaccines in allergen-specific immunotherapy to desensitize shellfish allergy patients and/or develop tolerance to shellfish in the recipients. Also, the MEM49-encoding DNA vaccine and MED171-encoding DNA vaccine can be used as prophylactic vaccines for the prevention of hypersensitivity responses to shellfish tropomyosin.

All patents, patent applications, and other publications, including GenBank Accession Numbers, cited in this application are incorporated by reference in the entirety for all purposes.

```
INFORMAL SEQUENCE LISTING

SEQ ID NO: 1
MEM49 coding sequence
ATGAAATTAGAGAAAGATAATGCGATGGACCGCGCTGATACCGCTGAGGGAGACAAAAAGGAGG
CCAATAACCGCGCAGAGAAGTCTGAAGAAGAATTAGTGGCGCTGCAGAAGAAATTGAAAGGCAC
CGAAGATGAACTGGATAAGTATCAGGAAAGCCTGCTGAAGGCTAATAATCAGTTAGTGGAGAAG
GATAAGGCGCTGAGCAATGCGGAAGGCGAAGTGGCGAGCCTGAATCGTCGTATTCAGCTGGTCG
AGGAAGAGCTGGATCGTGCACAGGAACGCTTAAATACCGCGACCACCAAACTGGCGGAAGCGAG
CCAAGCAGCAGACGAGAGCGAGCGTATGCGTAAAGTGCTTGAAAACCGTAGCCTGAGCGATGAA
GAACGTATGGATGCGCTGGAAATTCAGTTAAAAGAAGCGAAACATATTGCTGAGGAAGCGGATC
GTAAATATGAGGAGGTTGCGCGTAAACTTGCTATGGTGGAAGCAGATCTTGAACGGGCCGAGGA
GCGTGCTGAAACCGGGGAAAGCAAAATTAGCGAGCTTGAAGAGGAGTTGAAGACCGTGACGAAC
AATCTGAAAAGTCTGGAAGCGCAAGCTGAGAAAGCTAACCAGCGGGAGGAGGCGTATAAAGAAC
AGATTAAAACCCTGACCAATAAACTGAAAGCGGCAGAAACCCGTGCGGAATTTGCGGAACGTAG
CGTGGCGAAACTGGAAAAGACCATTGATGACCTGGAAGACGAACTGGTGAATGAAAAAGAGAAA
TACAAAGCGATTTCCGAAGAACTTGATCATGCACTGAATGATATGAGCGGCTAT SEQ ID NO: 2
MED171 coding sequence
ATGAAGCTGGAGAAGGATAACGCCATGGACAGGGCGGATACCGAGGCCAACAACAGGGCTGAGA
AGAGCGAGGAGGAGCAGGAATCCTTGCTGAAGGCAAACAACCAGCTCGTGGAGAAGGACAAGGC
CCTCTCTAACGCTGAGGGTGAGGTTGCTGAACGCCTCAACACCGCCACCACCAAGCTGGCTGAG
GCCTCCCAGGCCGCCGACGAGTCCGAGCGCATGCGCAAGGTGCTCGAGAACCGCTCCCTTTCCG
ATGAGGAGCGCATGGACGCCCTGGAGGCTGAGGAAGCCGACAGGGCCCGTAAGCTGGCCATGGT
TGAGGCCGACCTTGAGCGTGCTGAAGAACGTGCTGAGACTGGTGAATCAAAGATCGAGAAGGCT
AACCAACGCGAAGAGGCCTACAAGGAGCAGATCAAGACCCTGACCAACAAGCTGAAGGCGGCTT
TCGCCGAGAGGTCTGTGCTCGAAGACGAACTGGTTAACGAAAAGGAGAAGTACAAGTCTGGCTA
C SEQ ID NO: 3
MEM49 protein sequence
MKLEKDNAMDRADTAEGDKKEANNRAEKSEEELVALQKKLKGTEDELDKYQESLLKANNQLVEK
DKALSNAEGEVASLNRRIQLVEEELDRAQERLNTATTKLAEASQAADESERMRKVLENRSLSDE
ERMDALEIQLKEAKHIAEEADRKYEEVARKLAMVEADLERAEERAETGESKISELEEELKTVTN
NLKSLEAQAEKANQREEAYKEQIKTLTNKLKAAETRAEFAERSVAKLEKTIDDLEDELVNEKEK
YKAISEELDHALNDMSGY SEQ ID NO: 4
MED171 protein sequence
MKLEKDNAMDRADTEANNRAEKSEEEQESLLKANNQLVEKDKALSNAEGEVAERLNTATTKLAE
ASQAADESERMRKVLENRSLSDEERMDALEAEEADRARKLAMVEADLERAEERAETGESKIEKA
NQREEAYKEQIKTLTNKLKAAFAERSVLEDELVNEKEKYKSGY SEQ ID NO: 5
Met e 1 tropomyosin allergen of Metapenaeus ensis (Greasyback shrimp)
MKLEKDNAMDRADTLEQQNKEANNRAEKSEEEVHNLQKRMQQLENDLDQVQESLLKANNQLVEK
DKALSNAEGEVAALNRRIQLLEEDLERSEERLNTATTKLAEASQAADESERMRKVLENRSLSDE
ERMDALENQLKEARFLAEEADRKYDEVARKLAMVEADLERAEERAETGESKIVELEEELRVVGN
NLKSLEVSEEKANQREEAYKEQIKTLTNKLKAAEARAEFAERSVQKLQKEVDRLEDELVNEKEK
```

INFORMAL SEQUENCE LISTING

YKSITDELDQTFSELSGY

SEQ ID NO: 6
MEM49 forward primer
5'-CGCTCGAGGATATCATGAAATTA-3'

SEQ ID NO: 7
MEM49 reverse primer
5'-CGTCTAGAAAGCTTATAGCCG-3'

SEQ ID NO: 8
MED171 forward primer
5'-CGGAATTCGATATCATGAAGCTGG-3'

SEQ ID NO: 9
MED171 reverse primer
5'-CGTCTAGAAAGCTTGTAGCAG-3'

SEQ ID NO: 10
ISS-ODN
5'-TGACTGTGAACGTTCGAGATGA-'3

---

What is claimed is:

1. An isolated nucleic acid comprising a polynucleotide sequence encoding the polypeptide comprising the amino acid sequence set forth in SEQ ID NO:3 or 4.

2. The nucleic acid of claim 1, comprising the polynucleotide sequence set forth in SEQ ID NO:1 or 2.

3. An expression cassette comprising the nucleic acid of claim 1 operably linked to a promoter.

4. A vector comprising the nucleic acid of claim 1.

5. A host cell comprising the nucleic acid of claim 1.

6. A composition comprising (1) the nucleic acid of claim 1; and (2) a physiologically acceptable excipient.

7. The composition of claim 6, wherein the excipient is an adjuvant.

8. The composition of claim 6, further comprising an excipient suitable for oral administration.

9. The composition of claim 6, further comprising an excipient suitable for intradermal administration.

10. A method for reducing allergy in a subject, comprising administering to the subject a DNA vaccine comprising an effective amount of the nucleic acid of claim 1.

11. The method of claim 10, wherein the nucleic acid comprises the polynucleotide sequence set forth in SEQ ID NO:1 or 2.

12. The method of claim 10, wherein the subject is intradermally administered the DNA vaccine composition.

13. The method of claim 12, wherein the DNA vaccine comprises an adjuvant.

14. The method of claim 10, wherein the administering step is repeated twice or more to the subject.

15. A host cell comprising the expression cassette of claim 3.

16. A host cell comprising the vector of claim 4.

17. A composition comprising (1) the expression cassette of claim 3; and (2) a physiologically acceptable excipient.

18. A composition comprising (1) the vector of claim 4; and (2) a physiologically acceptable excipient.

19. A method for reducing allergy in a subject, comprising intradermally administering to the subject a DNA vaccine comprising an effective amount of the expression cassette of claim 3.

20. A method for reducing allergy in a subject, comprising intradermally administering to the subject a DNA vaccine comprising an effective amount of the vector of claim 4.

* * * * *